(12) United States Patent
Fennimore et al.

(10) Patent No.: US 9,947,872 B2
(45) Date of Patent: Apr. 17, 2018

(54) HOLE TRANSPORT MATERIALS

(71) Applicant: E I DU PONT DE NEMOURS AND COMPANY, Wilmington, DE (US)

(72) Inventors: Adam Fennimore, Wilmington, DE (US); Nora Sabina Radu, Landenberg, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 15/325,936

(22) PCT Filed: Jul. 2, 2015

(86) PCT No.: PCT/US2015/039019
§ 371 (c)(1),
(2) Date: Jan. 12, 2017

(87) PCT Pub. No.: WO2016/010746
PCT Pub. Date: Jan. 21, 2016

(65) Prior Publication Data
US 2017/0200893 A1  Jul. 13, 2017

Related U.S. Application Data

(60) Provisional application No. 62/024,509, filed on Jul. 15, 2014.

(51) Int. Cl.
*H01L 51/00* (2006.01)
*C08G 61/12* (2006.01)
(Continued)

(52) U.S. Cl.
CPC ........ *H01L 51/0035* (2013.01); *C07C 211/56* (2013.01); *C08G 61/128* (2013.01);
(Continued)

(58) Field of Classification Search
None
See application file for complete search history.

(56) References Cited

U.S. PATENT DOCUMENTS 4,720,432 A * 1/1988 VanSlyke ............... C09K 11/06
252/301.16
6,670,645 B2  12/2003 Grushin et al.
(Continued)

FOREIGN PATENT DOCUMENTS

JP  2007204574 A * 8/2007
WO  03008424 A1  1/2003
(Continued)

OTHER PUBLICATIONS

Machine translation of JP 2007-204574 A, retrieved Nov. 2017 (Year: 2017).*
(Continued)

*Primary Examiner* — Nicole M Buie-Hatcher

(57) ABSTRACT

There is disclosed a compound having Formula I

Formula I

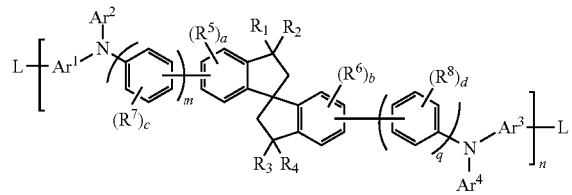

In Formula I: $Ar^1$ and $Ar^3$ are the same or different and are aryl groups; $Ar^2$ and $Ar^4$ are the same or different and are aryl groups; L is the same or different at each occurrence and can be H, D, halogen, aryl, arylamino, crosslinkable groups,
(Continued)

deuterated aryl, deuterated arylamino, or deuterated crosslinkable groups; $R^1$-$R^4$ are the same or different and can be H, D, alkyl, alkoxy, aryl, aryloxy, silyl, deuterated alkyl, deuterated alkoxy, deuterated aryl, deuterated aryloxy, or deuterated silyl; $R^5$-$R^8$ are the same or different and can be D, F, alkyl, aryl, alkoxy, aryloxy, silyl, crosslinkable groups, deuterated alkyl, deuterated alkoxy, deuterated aryl, deuterated aryloxy, or deuterated silyl, where adjacent $R^5$-$R^8$ groups can be joined together to form an aromatic ring; a and b are the same or different and are an integer from 0-3; c and d are the same or different at each occurrence and are an integer from 0-4; m and q are the same or different and are an integer from 1-6; and n is an integer greater than 0.

12 Claims, 1 Drawing Sheet

(51) Int. Cl.
    *C07C 211/56* (2006.01)
    *H01L 51/50* (2006.01)
(52) U.S. Cl.
    CPC ...... *H01L 51/0043* (2013.01); *C07C 2603/97* (2017.05); *C08G 2261/124* (2013.01); *C08G 2261/148* (2013.01); *C08G 2261/1412* (2013.01); *C08G 2261/228* (2013.01); *C08G 2261/314* (2013.01); *C08G 2261/3162* (2013.01); *C08G 2261/95* (2013.01); *H01L 51/5056* (2013.01)

(56) References Cited

U.S. PATENT DOCUMENTS

| | | | | |
|---|---|---|---|---|
| 7,318,966 | B2* | 1/2008 | Tominaga | C07C 15/28 257/40 |
| 8,487,055 | B2 | 7/2013 | Radu et al. | |
| 2003/0124382 | A1* | 7/2003 | Taguchi | C08G 61/12 428/690 |
| 2004/0102577 | A1 | 5/2004 | Hsu et al. | |
| 2004/0127637 | A1 | 7/2004 | Hsu et al. | |
| 2005/0184287 | A1 | 8/2005 | Herron et al. | |
| 2005/0205860 | A1 | 9/2005 | Hsu et al. | |
| 2007/0262703 | A1 | 11/2007 | Tsai et al. | |
| 2012/0046440 | A1* | 2/2012 | McKiernan | C08G 61/12 528/380 |

FOREIGN PATENT DOCUMENTS

| | | | |
|---|---|---|---|
| WO | 03040257 A1 | 5/2003 | |
| WO | 03063555 A1 | 7/2003 | |
| WO | 03091688 A2 | 11/2003 | |
| WO | 2004016710 A1 | 2/2004 | |
| WO | 2005052027 A1 | 6/2005 | |
| WO | 2007145979 A2 | 12/2007 | |
| WO | 2009067419 A1 | 5/2009 | |
| WO | WO-2012087930 A2* | 6/2012 | ........... C07C 211/61 |

OTHER PUBLICATIONS

Gustafsson: "Flexible light-emitting diodes made from soluble conducting polymer," Nature vol. 357, pp. 477 479.
Wang: "Pholoconfuctive Materials," Kirk Othmer Encyclopedia of Chemical Technology, vol. 18, pp. 837 860.
Chen: "Generation and Synthetic Uses of Stable 4[2-Isopropylidene]-phenol Carbocation from Bisphenol A," Org. Letters, vol. 6, pp. 2341-2343.
Liao: "Hole mobilities of 2,7-and 2,2' disubstituted 9,9'-spirobifulorene-based triaryldiamines and their application as hole transport materials in OLEDS," Chem Mater, vol. 19, pp. 6350-6357.
Gondek: Some spirobiindane based 1H-pyrazolo [3,4-b] quinolone chromophore as novel chromophore for light-emitting diodes, Journal of Luminescence, vol. 130, pp. 2093-2099 English Abstract Provided.
Written Opinion of the International Searching Authority, Korean Intellectual Property Office, Daejeon, Republic of Korea, in PCT/US2015/039019, PCT Counterpart of the Present Application, Present Application Number not assigned at time of IDS, Sep. 23, 2015.

* cited by examiner

HOLE TRANSPORT MATERIALS

BACKGROUND INFORMATION

Field of the Disclosure

The present disclosure relates to novel hole transport compounds. The disclosure further relates to electronic devices having at least one layer comprising such an hole transport compound.

Description of the Related Art

In organic electronic devices, such as organic light emitting diodes ("OLED"), that make up OLED displays, one or more organic electroactive layers are sandwiched between two electrical contact layers. In an OLED at least one organic electroactive layer emits light through the light-transmitting electrical contact layer upon application of a voltage across the electrical contact layers.

It is well known to use organic electroluminescent compounds as the light-emitting component in light-emitting diodes. Simple organic molecules, conjugated polymers, and organometallic complexes have been used.

Devices that use electroluminescent materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

There is a continuing need for electroactive materials for use in electronic devices.

SUMMARY

There is provided a compound having Formula I

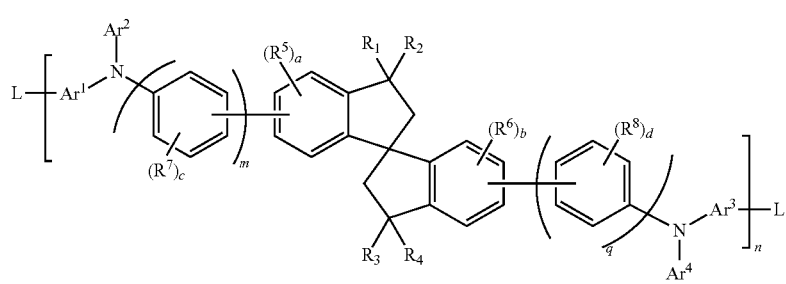

Formula I wherein:
  $Ar^1$ and $Ar^3$ are the same or different and are aryl groups;
  $Ar^2$ and $Ar^4$ are the same or different and are aryl groups;
  L is the same or different at each occurrence and is selected from the group consisting of H, D, halogen, aryl, arylamino, crosslinkable groups, deuterated aryl, deuterated arylamino, and deuterated crosslinkable groups;
  $R^1$-$R^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
  $R^5$-$R^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent $R^5$-$R^8$ groups can be joined together to form an aromatic ring;
  a and b are the same or different and are an integer from 0-3;
  c and d are the same or different at each occurrence and are an integer from 0-4;
  m and q are the same or different and are an integer from 1-6; and
  n is an integer greater than 0.

There is also provided a copolymer having at least one monomeric unit of Formula I-m Formula I-m

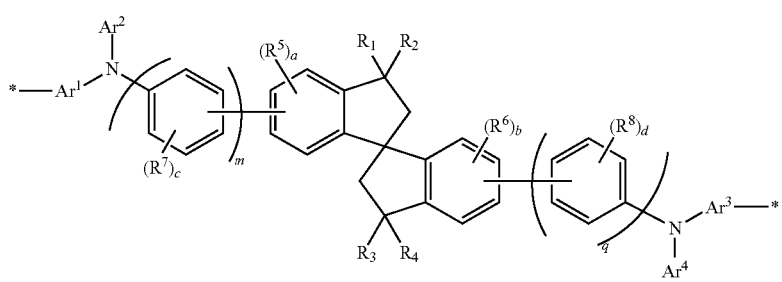

wherein:
Ar¹ and Ar³ are the same or different and are aryl groups;
Ar² and Ar⁴ are the same or different and are aryl groups;
$R^1$-$R^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
$R^5$-$R^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent $R^5$-$R^8$ groups can be joined together to form an aromatic ring;
a and b are the same or different and are an integer from 0-3;
c and d are the same or different at each occurrence and are an integer from 0-4;
m and q are the same or different and are an integer from 1-6; and
* represents the point of attachment in the copolymer.

There is also provided an electronic device having at least one layer comprising a compound or copolymer.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
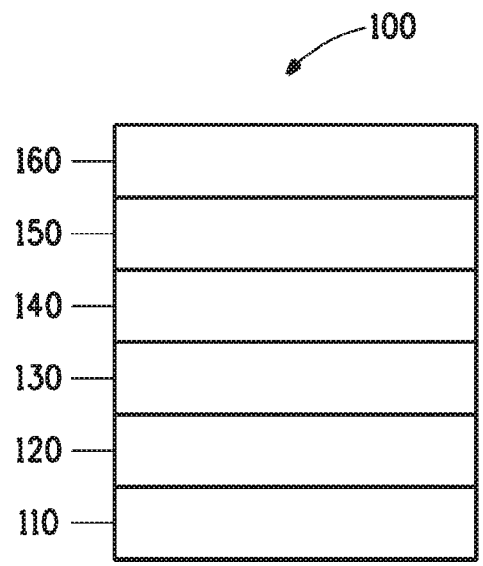
FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided a compound having Formula I

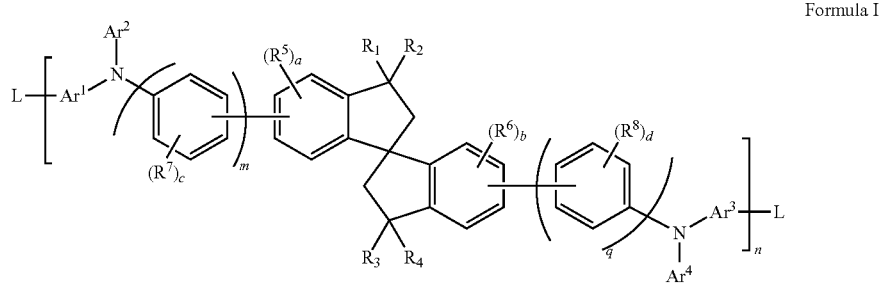

Formula I wherein:
Ar¹ and Ar³ are the same or different and are aryl groups;
Ar² and Ar⁴ are the same or different and are aryl groups;
L is the same or different at each occurrence and is selected from the group consisting of H, D, halogen, aryl, arylamino, crosslinkable groups, deuterated aryl, deuterated arylamino, and deuterated crosslinkable groups;
$R^1$-$R^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
$R^5$-$R^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent $R^5$-$R^8$ groups can be joined together to form an aromatic ring;
a and b are the same or different and are an integer from 0-3;
c and d are the same or different at each occurrence and are an integer from 0-4;
m and q are the same or different and are an integer from 1-6; and
n is an integer greater than 0.

There is further provided a copolymer having at least one monomeric unit of Formula I-m

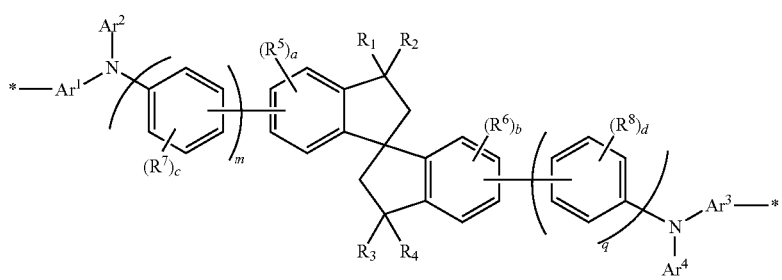

Formula I-m wherein:
Ar$^1$ and Ar$^3$ are the same or different and are aryl groups;
Ar$^2$ and Ar$^4$ are the same or different and are aryl groups;
R$^1$-R$^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
R$^5$-R$^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent R$^5$-R$^8$ groups can be joined together to form an aromatic ring;
a and b are the same or different and are an integer from 0-3;
c and d are the same or different at each occurrence and are an integer from 0-4;
m and q are the same or different and are an integer from 1-6; and
* represents the point of attachment in the copolymer.

There is further provided an electronic device having at least one layer comprising a compound having Formula I or a copolymer having at least one monomeric unit having Formula I-m.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compound, the Copolymer, the Electronic Device, and finally Examples.

1. Definitions and Clarification of Terms

Before addressing details of embodiments described below, some terms are defined or clarified.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tertbutyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aromatic compound" is intended to mean an organic compound comprising at least one unsaturated cyclic group having delocalized pi electrons. The term is intended to encompass both aromatic compounds having only carbon and hydrogen atoms, and heteroaromatic compounds wherein one or more of the carbon atoms within the cyclic group has been replaced by another atom, such as nitrogen, oxygen, sulfur, or the like.

The term "aryl" or "aryl group" means a moiety derived from an aromatic compound. The aryl group may be a single ring (monocyclic) or multiple rings (bicyclic, or more) fused together or linked covalently. Examples of aryl moieties include, but are not limited to, phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments, aryl groups have 6 to 60 ring carbon atoms; in some embodiments, 6 to 30 ring carbon atoms. The term is intended to include heteroaryl groups. Heteroaryl groups may have from 4-50 ring carbon atoms; in some embodiments, 4-30 ring carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include D, alkyl, aryl, nitro, cyano, —N(R$^7$)(R$^8$), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxane, thioalkoxy, —S(O)$_2$—N(R')(R"), —C(=O)—N(R')(R"), (R')(R")N-alkyl, (R')(R")N-alkoxyalkyl, (R')(R")N-alkylaryloxyalkyl, —S(O)$_s$-aryl (where s=0-2) or —S(O)$_s$-heteroaryl (where s=0-2). Each R' and R" is independently an optionally substituted alkyl, cycloalkyl, or aryl group. R' and R", together with the nitrogen atom to which they are bound, can form a ring system in certain embodiments. Substituents may also be crosslinking groups.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "crosslinkable group" or "crosslinking group" is intended to mean a group on a compound or polymer chain than can link to another compound or polymer chain via thermal treatment, use of an initiator, or exposure to radiation, where the link is a covalent bond. In some embodiments, the radiation is UV or visible. Examples of crosslinkable groups include, but are not limited to vinyl, acrylate, perfluorovinylether, 1-benzo-3,4-cyclobutane, o-quinodimethane groups, siloxane, cyanate groups, cyclic ethers (epoxides), cycloalkenes, and acetylenic groups.

The term "electroactive" as it refers to a layer or a material, is intended to indicate a layer or material which electronically facilitates the operation of the device. Examples of electroactive materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The prefix "fluoro" is intended to indicate that one or more hydrogens in a group has been replaced with fluorine.

The prefix "hetero" indicates that one or more carbon atoms has been replaced with a different atom. In some embodiments, the heteroatom is O, N, S, or combinations thereof.

The term "liquid composition" is intended to mean a liquid medium in which a material is dissolved to form a solution, a liquid medium in which a material is dispersed to form a dispersion, or a liquid medium in which a material is suspended to form a suspension or an emulsion.

The term "photoactive" refers to a material or layer that emits light when activated by an applied voltage (such as in a light emitting diode or chemical cell), that emits light after the absorption of photons (such as in down-converting phosphor devices), or that responds to radiant energy and generates a signal with or without an applied bias voltage (such as in a photodetector or a photovoltaic cell).

The term "silyl" refers to the group $R_3Si—$, where R is H, D, C1-20 alkyl, fluoroalkyl, or aryl. In some embodiments, one or more carbons in an R alkyl group are replaced with Si. In some embodiments, the silyl groups are $(hexyl)_2Si(Me)CH_2CH_2Si(Me)_2$- and $[CF_3(CF_2)_6CH_2CH_2]_2SiMe$-.

The term "siloxane" refers to the group $(RO)_3Si—$, where R is H, D, C1-20 alkyl, or fluoroalkyl.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, $81^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Compound

The compound described herein has Formula I

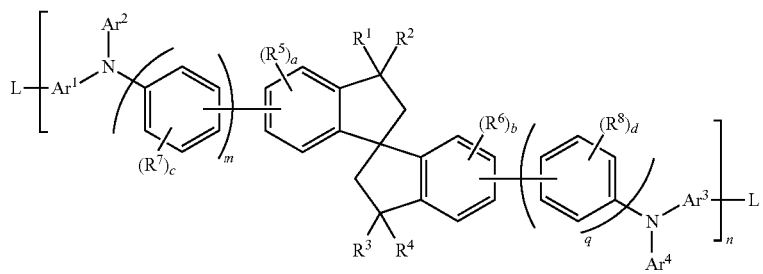

Formula I wherein:
Ar$^1$ and Ar$^3$ are the same or different and are aryl groups;
Ar$^2$ and Ar$^4$ are the same or different and are aryl groups;
L is the same or different at each occurrence and is selected from the group consisting of H, D, halogen, aryl, arylamino, crosslinkable groups, deuterated aryl, deuterated arylamino, and deuterated crosslinkable groups;
R$^1$-R$^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
R$^5$-R$^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent R$^5$-R$^8$ groups can be joined together to form an aromatic ring;
a and b are the same or different and are an integer from 0-3;
c and d are the same or different at each occurrence and are an integer from 0-4;
m and q are the same or different and are an integer from 1-6; and
n is an integer greater than 0.

The compound having Formula I can be a small molecule with n=1, an oligomer, or a polymer. As used herein, the term "compound having Formula I" is intended to include small molecules, oligomers and polymers.

In some embodiments of Formula I, n=1 and L is halogen. Such compounds can be useful as monomers for the formation of polymeric compounds. In some embodiments, the halogen is Cl or Br; in some embodiments, Br.

In some embodiments of Formula I, n=1 and L is a crosslinking group or deuterated crosslinking group.

In some embodiments of Formula I, n=1 and L is H or D.

In some embodiments of Formula I, n=2-10.

In some embodiments of Formula I, the compound is a polymer with n>10. In some embodiments, the compound is a polymer with $M_n$>20,000; in some embodiments, $M_n$>50,000.

In some embodiments of Formula I, n>10 and L is selected from aryl, arylamino, crosslinkable groups, and deuterated analogs thereof.

In some embodiments of Formula I, n>10 and L is selected from phenyl, triphenylamino, and deuterated analogs thereof.

In some embodiments, the compound having Formula I is deuterated. The term "deuterated" is intended to mean that at least one H has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level. In some embodiments, the compound is at least 10% deuterated. By "% deuterated" or "% deuteration" is meant the ratio of deuterons to the sum of protons plus deuterons, expressed as a percentage. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

Deuterated materials can be less susceptible to degradation by holes, electrons, excitons, or a combination thereof. Deuteration can potentially inhibit degradation of the compound during device operation, which in turn can lead to improved device lifetime. In general, this improvement is accomplished without sacrificing other device properties. Furthermore, the deuterated compounds frequently have greater air tolerance than the non-deuterated analogs. This can result in greater processing tolerance both for the preparation and purification of the materials and in the formation of electronic devices using the materials.

In some embodiments, one or more of Ar$^1$-Ar$^4$ is an aryl group having at least one fused ring.

In some embodiments, one or more of Ar$^1$-Ar$^4$ is selected from the group consisting of naphthyl, anthracenyl, naphthylphenyl, phenylnaphthyl, fluorenyl, substituted derivatives thereof, and deuterated analogs thereof.

In some embodiments of Formula I, Ar$^1$-Ar$^4$ are aryl groups having no fused rings.

In some embodiments of Formula I, Ar$^1$ has Formula a

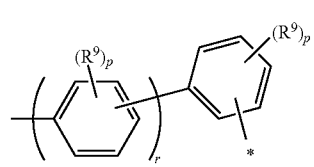

Formula a where:
R$^9$ is the same or different at each occurrence and is selected from the group consisting of D, alkyl, alkoxy, siloxane and silyl;

p is the same or different at each occurrence and is an integer from 0-4;
r is an integer from 1 to 5; and
* indicates the point of attachment to L.

In some embodiments, $Ar^1$ has Formula b

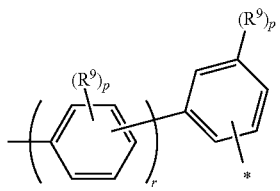

Formula b where $R^9$, p, r and * are as in Formula a.

In some embodiments of Formula I, $Ar^1$ has Formula c

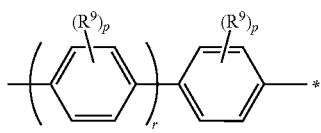

Formula c where $R^9$, p, r and * are as in Formula a.

In some embodiments of Formula I, $Ar^1$ is selected from the group consisting of 1-naphthyl, 2-naphthyl, anthracenyl, fluorenyl, deuterated analogs thereof, and derivatives thereof having one or more substituents selected from the group consisting of fluoro, alkyl, alkoxy, silyl, siloxy, a substituent with a crosslinking group, and deuterated analogs thereof.

In some embodiments of Formula I, $Ar^3$ has Formula a.
In some embodiments of Formula I, $Ar^3$ has Formula b.
In some embodiments of Formula I, $Ar^3$ has Formula c.
In some embodiments of Formula I, $Ar^3$ is selected from the group consisting of 1-naphthyl, 2-naphthyl, anthracenyl, fluorenyl, deuterated analogs thereof, and derivatives thereof having one or more substituents selected from the group consisting of fluoro, alkyl, alkoxy, silyl, siloxy, a substituent with a crosslinking group, and deuterated analogs thereof.

In some embodiments of Formulae a-c, at least one p is not zero.

In some embodiments of Formulae a-c, r=1-3.
In some embodiments of Formula I, $Ar^1$=$Ar^3$.
In some embodiments of Formula I, $Ar^1$ and $Ar^3$ are selected from the group consisting of phenyl, biphenyl, terphenyl, deuterated analogs thereof, and derivatives thereof having one or more substituents selected from the group consisting of fluoro, alkyl, alkoxy, silyl, siloxy, a substituent with a crosslinking group, and deuterated analogs thereof.

In some embodiments of Formula I, $Ar^2$ has Formula d

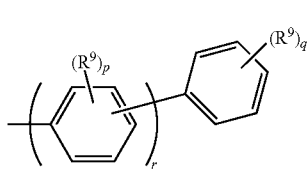

Formula d where:
$R^9$ is the same or different at each occurrence and is selected from the group consisting of D, alkyl, alkoxy, siloxane and silyl;
p is the same or different at each occurrence and is an integer from 0-4;
q is an integer from 0-5; and
r is an integer from 1 to 5.

In some embodiments, $Ar^2$ has Formula e

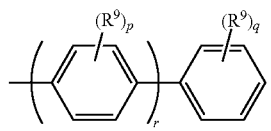

Formula e where $R^9$, p, q, and r are as in Formula d.

In some embodiments of Formula I, $Ar^2$ is selected from the group consisting of 1-naphthyl, 2-naphthyl, anthracenyl, fluorenyl, deuterated analogs thereof, and derivatives thereof having one or more substituents selected from the group consisting of fluoro, alkyl, alkoxy, silyl, siloxy, a substituent with a crosslinking group, and deuterated analogs thereof.

In some embodiments of Formula I, $Ar^4$ has Formula d.
In some embodiments of Formula I, $Ar^4$ has Formula e.
In some embodiments of Formula I, $Ar^4$ is selected from the group consisting of 1-naphthyl, 2-naphthyl, anthracenyl, fluorenyl, deuterated analogs thereof, and derivatives thereof having one or more substituents selected from the group consisting of fluoro, alkyl, alkoxy, silyl, siloxy, a substituent with a crosslinking group, and deuterated analogs thereof.

In some embodiments of Formulae d and e, at least one of p and q is not zero.

In some embodiments of Formulae d and e, r=1-3.
In some embodiments of Formula I, $Ar^2$=$Ar^4$.
In some embodiments of Formula I, $Ar^2$ and $Ar^4$ are selected from the group consisting of phenyl, biphenyl, terphenyl, deuterated analogs thereof, and derivatives thereof having one or more substituents selected from the group consisting of fluoro, alkyl, alkoxy, silyl, siloxy, a substituent with a crosslinking group, and deuterated analogs thereof.

In some embodiments of Formula I, $R^1$=$R^2$.
In some embodiments of Formula I, $R^1$≠$R^2$.
In some embodiments of Formula I, $R^3$=$R^4$.
In some embodiments of Formula I, $R^3$≠$R^4$.
In some embodiments of Formula I, $R^1$=$R^2$=$R^3$=$R^4$.
In some embodiments of Formula I, one or more $R^1$-$R^4$ are alkyl groups or deuterated alkyl groups. In some embodiments, the alkyl groups have 1-10 carbons; in some embodiments, 1-5 carbons.

In some embodiments of Formula I, one or more $R^1$-$R^4$ are methyl or deuterated methyl.

In some embodiments of Formula I, one or more $R^1$-$R^4$ are aryl groups or deuterated aryl groups. In some embodiments, the aryl or deuterated aryl groups have 4-20 ring carbons; in some embodiments, 6-12 ring carbons.

In some embodiments of Formula I, one or more $R^1$-$R^4$ are selected from the group consisting of phenyl, biphenyl, substituted derivatives thereof, and deuterated analogs thereof.

In some embodiments of Formula I, one or more $R^1$-$R^4$ are silyl groups or deuterated silyl groups. In some embodiments, the silyl or deuterated silyl groups have 1-10 carbons; in some embodiments, 3-6 carbons.

In some embodiments of Formula I, one or more $R^1$-$R^4$ are trimethyl silyl or deuterated trimethyl silyl.

In some embodiments of Formula I, a=0.
In some embodiments of Formula I, a=1.
In some embodiments of Formula I, a=2.
In some embodiments of Formula I, a>0 and $R^5$ is D or $C_{1-10}$ alkyl.

In some embodiments, the alkyl group is deuterated.
In some embodiments of Formula I, a>0 and $R^5$ is $C_{1-10}$ silyl. In some embodiments, the silyl group is deuterated.

In some embodiments of Formula I, a>0 and $R^5$ is $C_{6-20}$ aryl or $C_{6-20}$ deuterated aryl. In some embodiments, the aryl group is a hydrocarbon aryl. In some embodiments, the aryl is a heteroaryl.

In some embodiments of Formula I, a=3 and $R^5$=D.
In some embodiments of Formula I, b=0.
In some embodiments of Formula I, b=1.
In some embodiments of Formula I, b=2.
In some embodiments of Formula I, b>0 and $R^6$ is D or $C_{1-10}$ alkyl.

In some embodiments, the alkyl group is deuterated.
In some embodiments of Formula I, b>0 and $R^6$ is $C_{1-10}$ silyl. In some embodiments, the silyl group is deuterated.

In some embodiments of Formula I, b>0 and $R^6$ is $C_{6-20}$ aryl or
$C_{6-20}$ deuterated aryl. In some embodiments, the aryl group is a hydrocarbon aryl. In some embodiments, the aryl is a heteroaryl.

In some embodiments of Formula I, b=3 and $R^6$=D.
In some embodiments of Formula I, m=1.
In some embodiments of Formula I, m=2.
In some embodiments of Formula I, m=3.
In some embodiments of Formula I, m=4.
In some embodiments of Formula I, m=5.
In some embodiments of Formula I, m=6.
In some embodiments of Formula I, m>1.
In some embodiments of Formula I, all c=0.
In some embodiments of Formula I, at least one c is greater than 0 and one or more $R^7$ are alkyl groups or deuterated alkyl groups. In some embodiments, the alkyl or deuterated alkyl groups have 1-10 carbons; in some embodiments, 1-5 carbons.

In some embodiments of Formula I, at least one c is greater than 0 and one or more $R^7$ are methyl or deuterated methyl.

In some embodiments of Formula I, at least one c is greater than 0 and one or more $R^7$ are aryl groups or deuterated aryl groups. In some embodiments, the aryl groups have 4-20 ring carbons; in some embodiments, 6-12 ring carbons.

In some embodiments of Formula I, at least one c is greater than 0 and one or more $R^7$ are selected from the group consisting of phenyl, biphenyl, substituted derivatives thereof, and deuterated analogs thereof.

In some embodiments of Formula I, at least one c is greater than 0 and one or more $R^7$ are silyl groups or deuterated silyl groups. In some embodiments, the silyl groups or deuterated silyl groups have 1-10 carbons; in some embodiments, 1-5 carbons.

In some embodiments of Formula I, at least one c is greater than 0 and one or more $R^7$ are trimethyl silyl or deuterated trimethyl silyl.

In some embodiments of Formula I, q=1.
In some embodiments of Formula I, q=2.
In some embodiments of Formula I, q=3.
In some embodiments of Formula I, q=4.
In some embodiments of Formula I, q=5.
In some embodiments of Formula I, q=6.
In some embodiments of Formula I, q>1.
In some embodiments of Formula I, all d=0.
In some embodiments of Formula I, at least one d is greater than 0 and one or more $R^8$ are alkyl groups or deuterated alkyl groups. In some embodiments, the alkyl or deuterated alkyl groups have 1-10 carbons; in some embodiments, 1-5 carbons.

In some embodiments of Formula I, at least one d is greater than 0 and one or more $R^8$ are methyl or deuterated methyl.

In some embodiments of Formula I, at least one d is greater than 0 and one or more $R^8$ are aryl groups or deuterated aryl groups. In some embodiments, the aryl groups have 4-20 ring carbons; in some embodiments, 6-12 ring carbons.

In some embodiments of Formula I, at least one d is greater than 0 and one or more $R^8$ are selected from the group consisting of phenyl, biphenyl, substituted derivatives thereof, and deuterated analogs thereof.

In some embodiments of Formula I, at least one d is greater than 0 and one or more $R^8$ are silyl groups or deuterated silyl groups. In some embodiments, the silyl groups or deuterated silyl groups have 1-10 carbons; in some embodiments, 1-5 carbons.

In some embodiments of Formula I, at least one d is greater than 0 and one or more $R^8$ are trimethyl silyl or deuterated trimethyl silyl.

In some embodiments, the compound having Formula I is further defined by Formula I-a Formula I-a

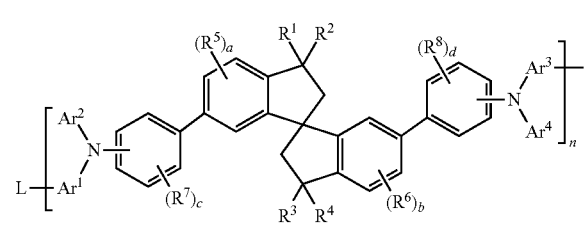

wherein:
$Ar^1$ and $Ar^3$ are the same or different and are aryl groups;
$Ar^2$ and $Ar^4$ are the same or different and are aryl groups;
L is the same or different at each occurrence and is selected from the group consisting of H, D, halogen, aryl, arylamino, crosslinkable groups, deuterated aryl, deuterated arylamino, and deuterated crosslinkable groups;
$R^1$-$R^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
$R^5$-$R^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent $R^5$-$R^8$ groups can be joined together to form an aromatic ring;
a and b are the same or different and are an integer from 0-3;
c and d are the same or different at each occurrence and are an integer from 0-4; and
n is an integer greater than 0.

The compound having Formula I-a can be a small molecule with n=1, an oligomer, or a polymer. In some embodiments, the compound is a polymer with $M_n>20,000$; in some embodiments, $M_n>50,000$.

All of the embodiments for $Ar^1$-$Ar^4$, L, $R^1$-$R^8$, a-d and n described above for Formula I, apply to Formula I-a as well.

In some embodiments, the compound having Formula I is further defined by Formula I-b

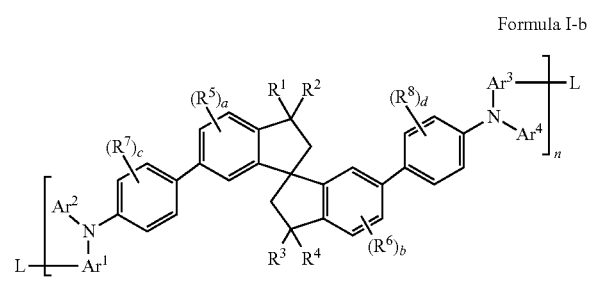

Formula I-b wherein:
$Ar^1$ and $Ar^3$ are the same or different and are aryl groups;
$Ar^2$ and $Ar^4$ are the same or different and are aryl groups;
L is the same or different at each occurrence and is selected from the group consisting of H, D, halogen, aryl, arylamino, crosslinkable groups, deuterated aryl, deuterated arylamino, and deuterated crosslinkable groups;
$R^1$-$R^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
$R^5$-$R^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent $R^5$-$R^8$ groups can be joined together to form an aromatic ring;
a and b are the same or different and are an integer from 0-3;
c and d are the same or different at each occurrence and are an integer from 0-4; and
n is an integer greater than 0.

The compound having Formula I-b can be a small molecule with n=1, an oligomer, or a polymer. In some embodiments, the compound is a polymer with $M_n>20,000$; in some embodiments, $M_n>50,000$.

All of the embodiments for $Ar^1$-$Ar^4$, L, $R^1$-$R^8$, a-d and n described above for Formula I, apply to Formula I-b as well.

In some embodiments, the compound having Formula I is further defined by Formula I-c wherein:
$Ar^1$ and $Ar^3$ are the same or different and are aryl groups;
$Ar^2$ and $Ar^4$ are the same or different and are aryl groups;
L is the same or different at each occurrence and is selected from the group consisting of H, D, halogen, aryl, arylamino, crosslinkable groups, deuterated aryl, deuterated arylamino, and deuterated crosslinkable groups;
$R^1$-$R^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
$R^5$-$R^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent $R^5$-$R^8$ groups can be joined together to form an aromatic ring;
a and b are the same or different and are an integer from 0-3;
c and d are the same or different at each occurrence and are an integer from 0-4; and
n is an integer greater than 0.

The compound having Formula I-c can be a small molecule with n=1, an oligomer, or a polymer. In some embodiments, the compound is a polymer with $M_n>20,000$; in some embodiments, $M_n>50,000$.

All of the embodiments for $Ar^1$-$Ar^4$, L, $R^1$-$R^8$, a-d and n described above for Formula I, apply to Formula I-c as well.

Any of the above embodiments for Formula I can be combined with one or more of the other embodiments, so long as they are not mutually exclusive. For example, the embodiment in which $Ar^1=Ar^3$ can be combined with the embodiment in which the compound has Formula I-c. The same is true for the other non-mutually-exclusive embodiments discussed above. The skilled person would understand which embodiments were mutually exclusive and would thus readily be able to determine the combinations of embodiments that are contemplated by the present application.

Some non-limiting examples of compounds having Formula I are shown below.

Formula I-c

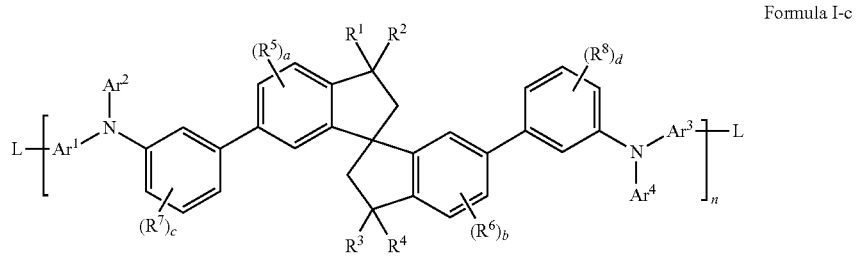

Compound H1
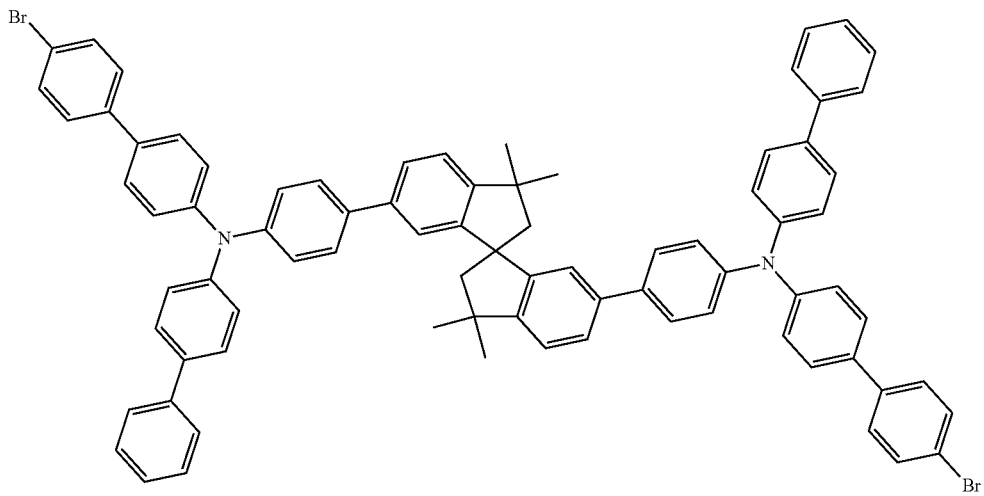
Compound H2
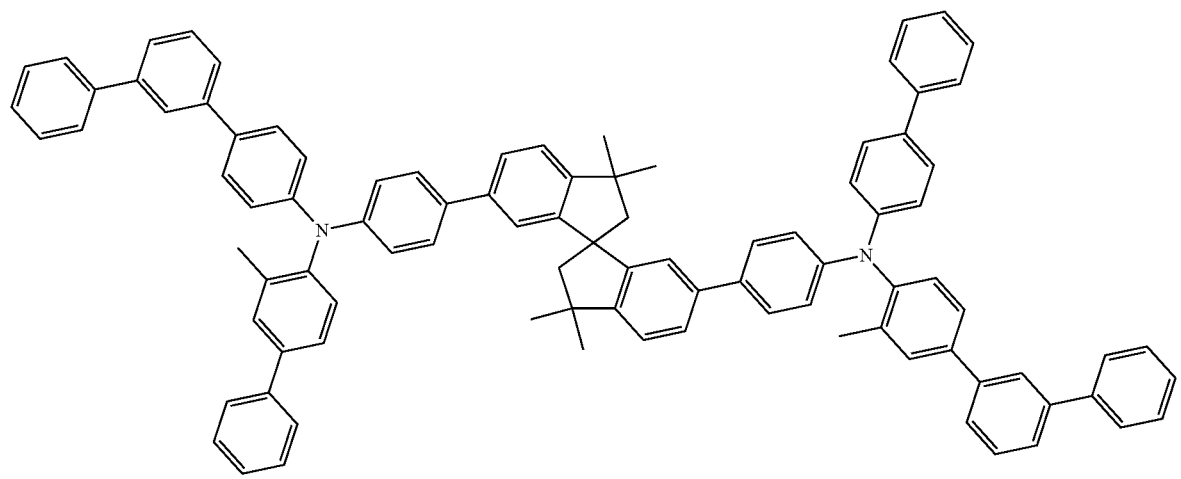
Compound H3
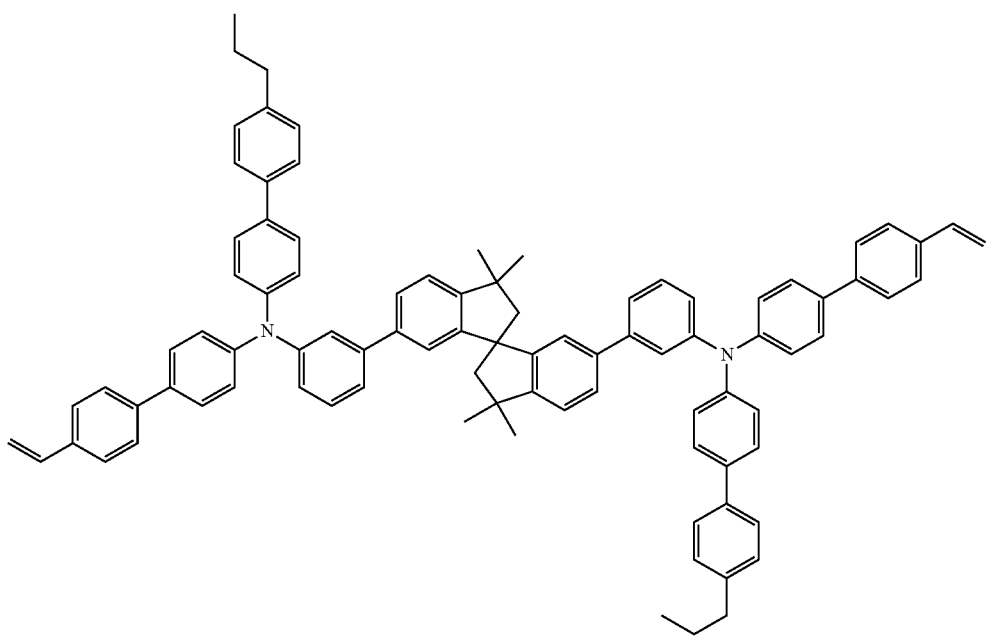

-continued
Compound H4
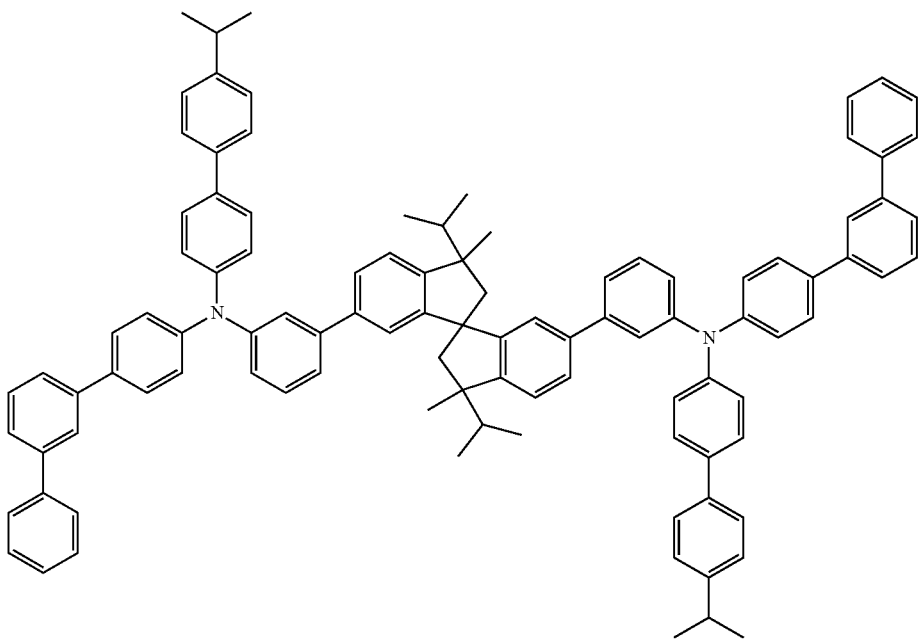
Compound H5
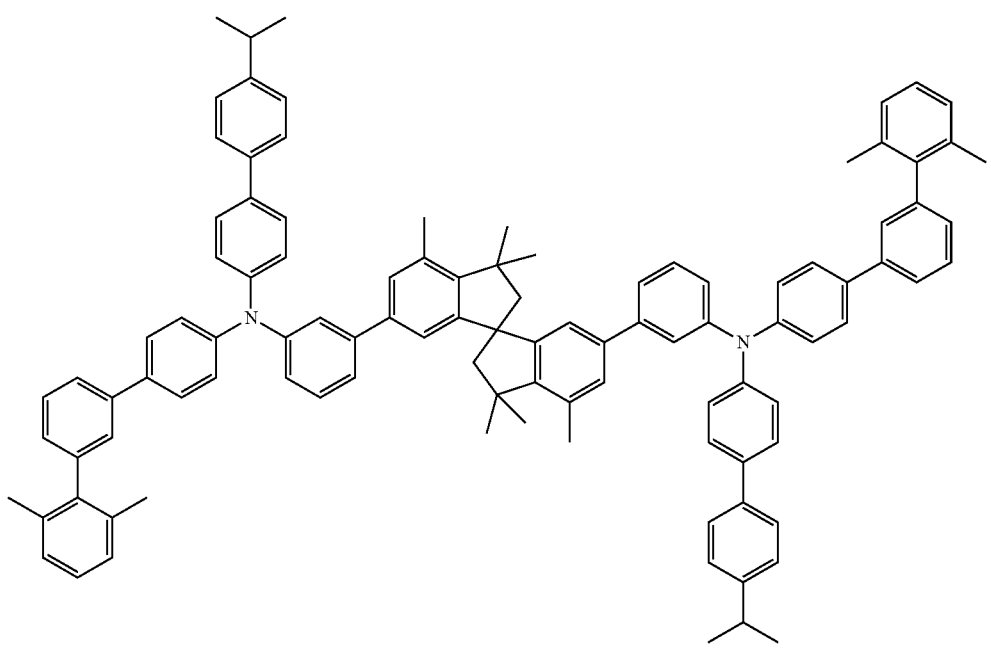

Compound H6
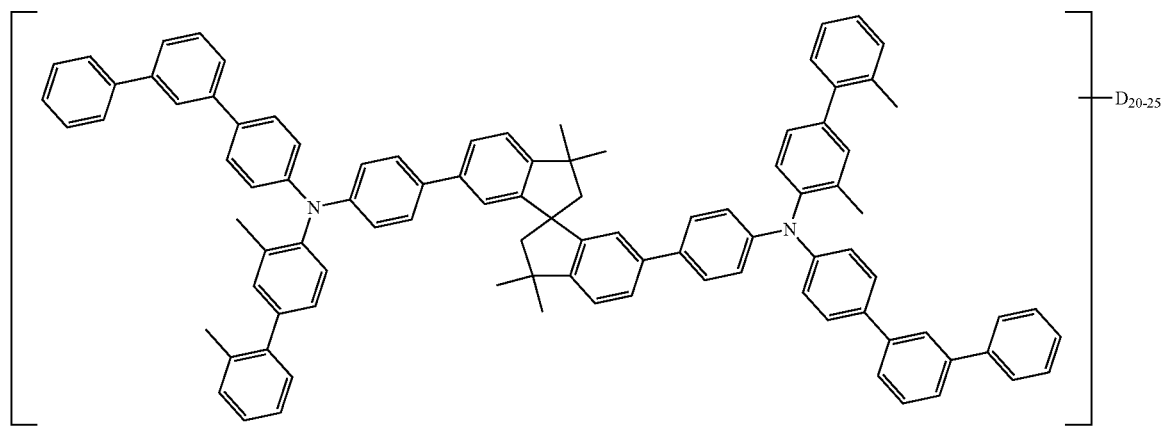
Compound H7
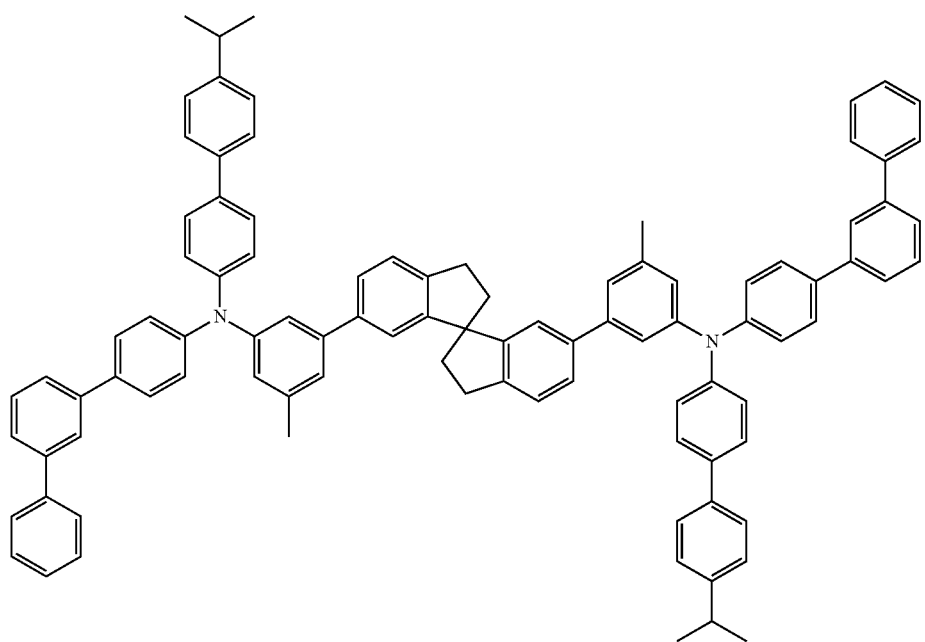

Compound H8
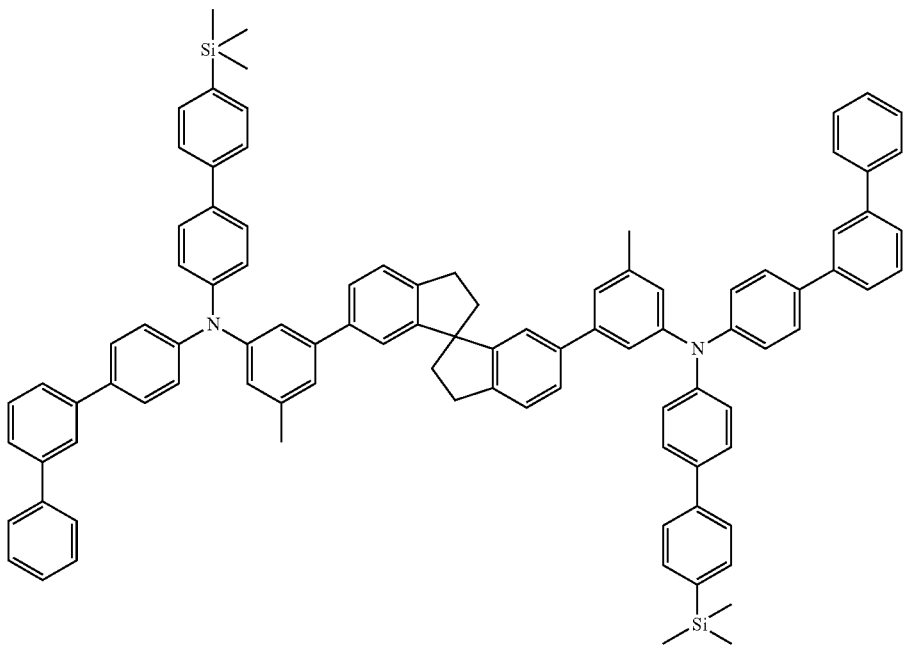
Compound H9
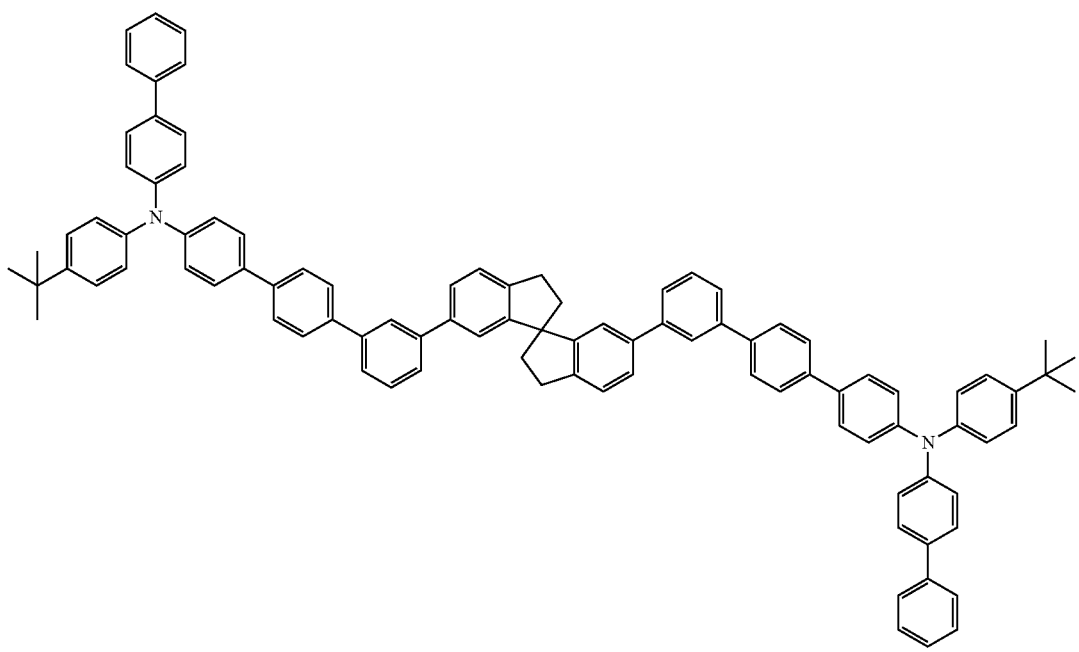

-continued
Compound H10
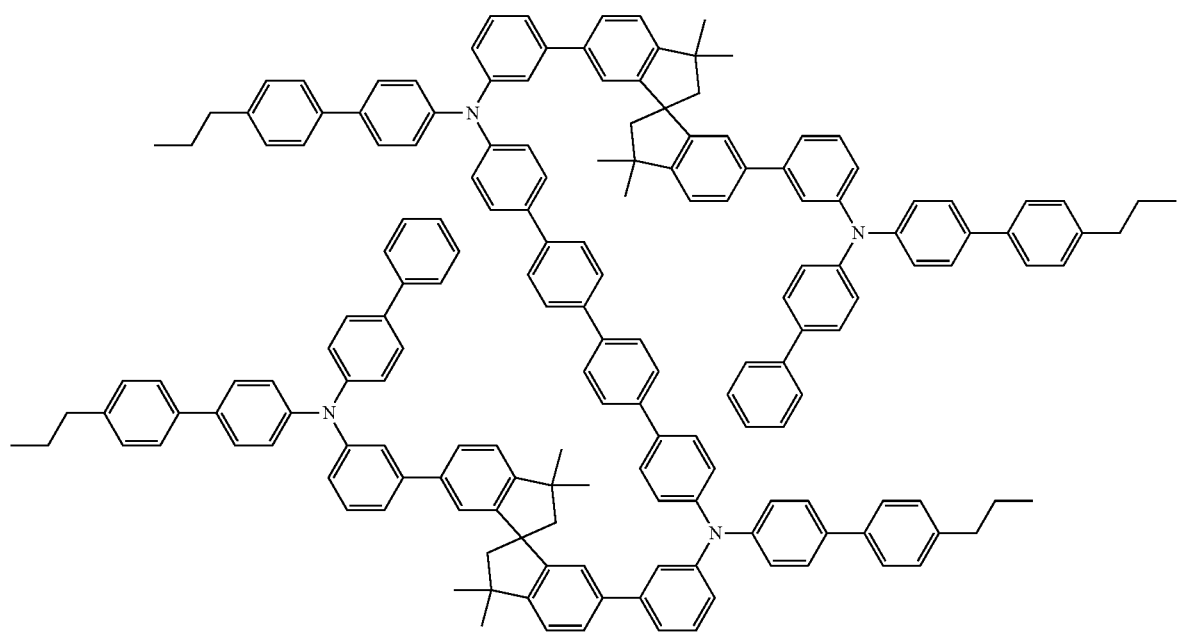
Compound H11
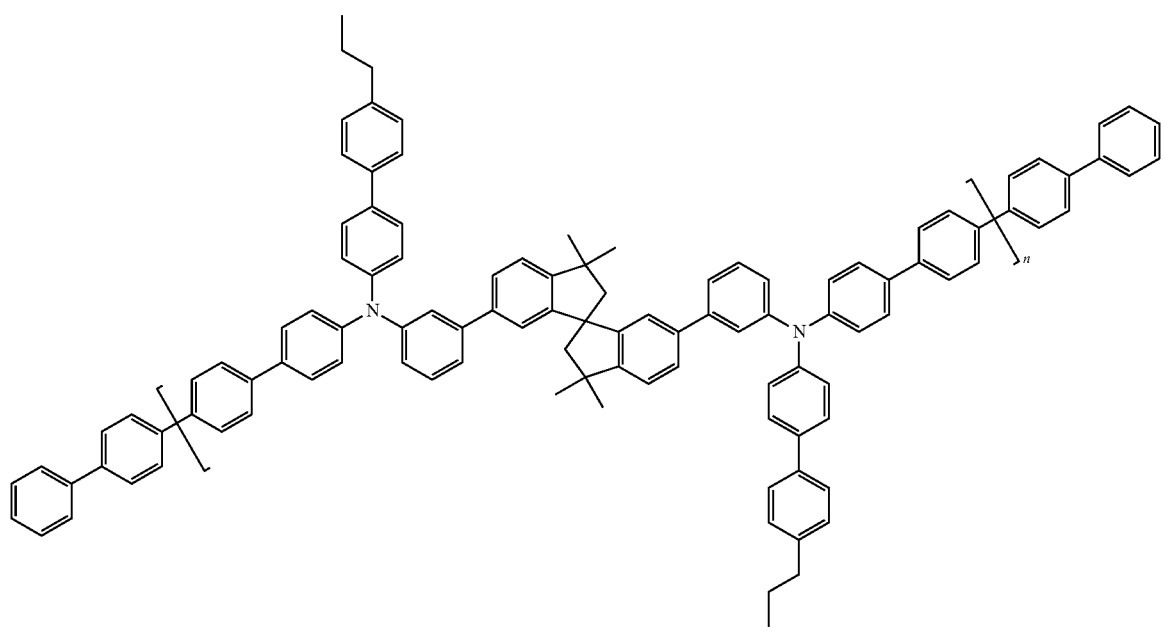

Compound H12
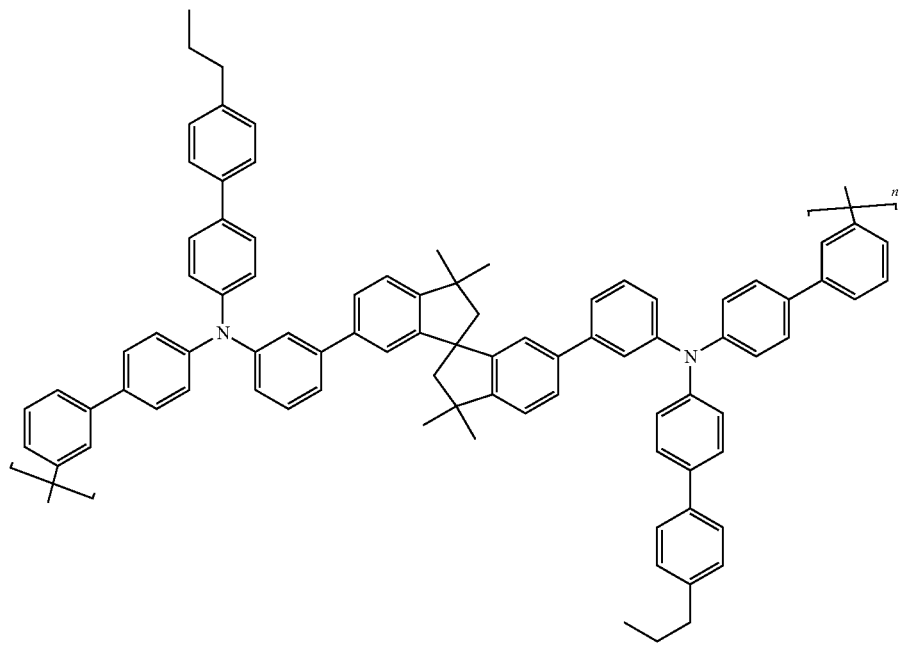
Compound H13
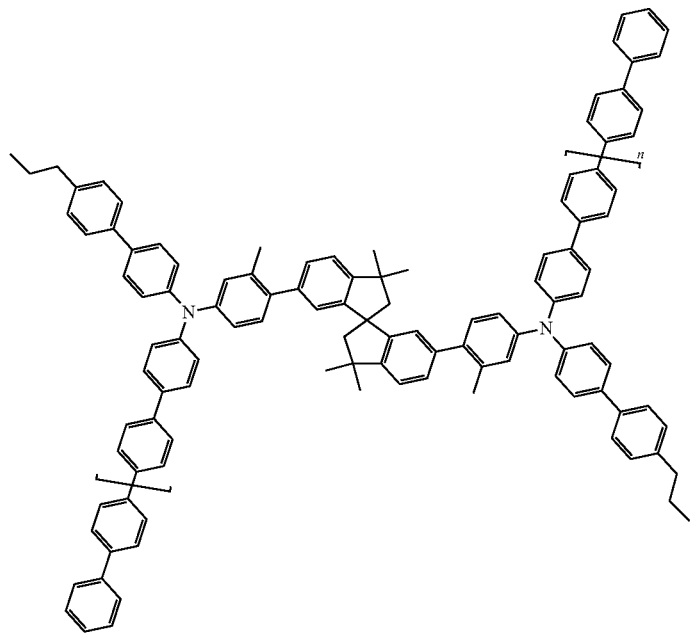

Compound H14
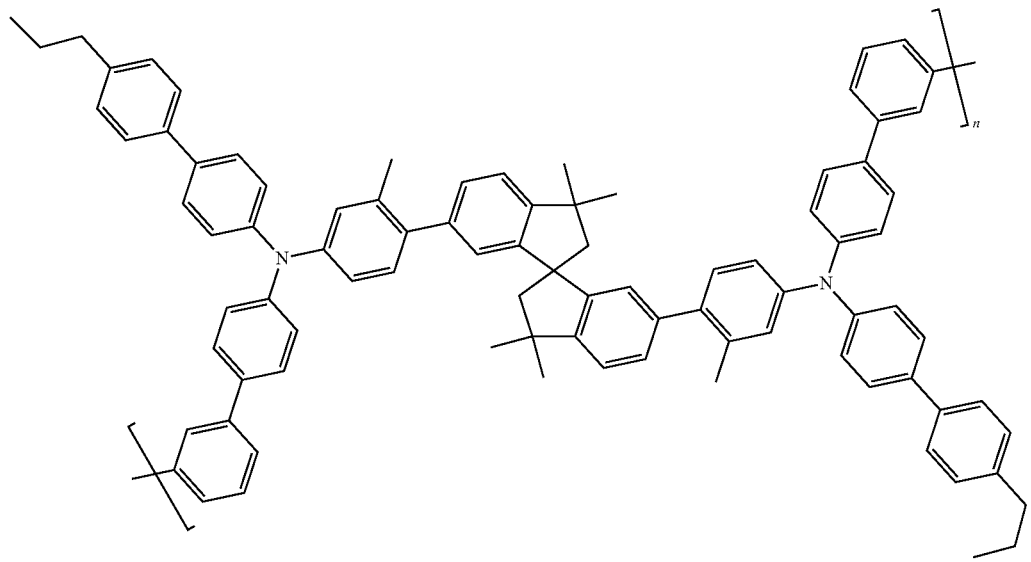
Compound H15
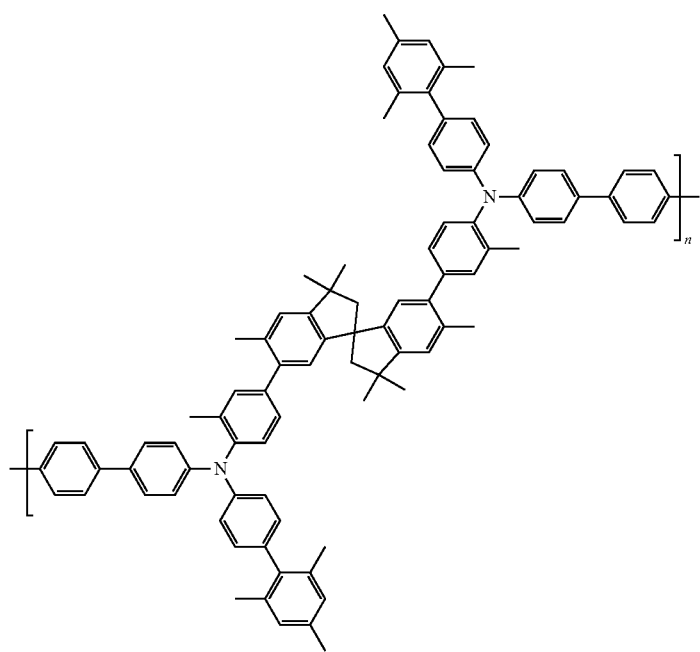

-continued

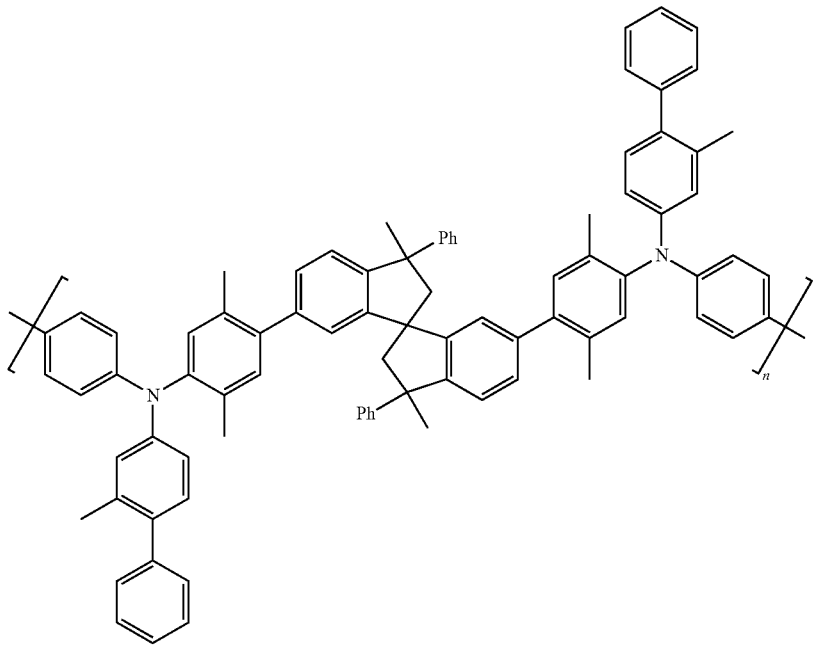

Compound H16

The new compounds can be made using any technique that will yield a C—C or C—N bond. A variety of such techniques are known, such as Suzuki, Yamamoto, Stille, and Pd- or Ni-catalyzed C—N couplings. Deuterated compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum dichloride. Exemplary preparations are given in the Examples.

The compounds can be formed into layers using solution processing techniques. The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer.

Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The new compounds having Formula I can be used as hole transport materials and as hosts for electroluminescent materials. The new compounds also have utility as materials for a priming layer to improve the deposition of a hole transport layer.

The new compounds having Formula I have at least one phenyl group between the spiro bis-indane group and the amino nitrogen. This has been found to result in an increase in the triplet energy and a deeper HOMO level. This results in the enhancement of hole injection and in minimizing quenching of emission from phosphorescent materials when the compound is in the same or an adjacent layer of a device. This also makes the materials of Formula I more suitable for use with blue emissive materials, as well as for green and red emissive materials The new compounds having Formula I have hole mobilities similar to efficient small molecule hole transport compounds such as N,N'-diphenyl-N,N'-bis(3-methylphenyl)-[1,1'-biphenyl]-4,4'-diamine (TPD). Compounds such as TPD generally must be applied using a vapor deposition technique, while the compounds having Formula I can be designed to be applied by liquid deposition.

3. Copolymers

The copolymer has at least one monomeric unit of Formula I-m

Formula I-m

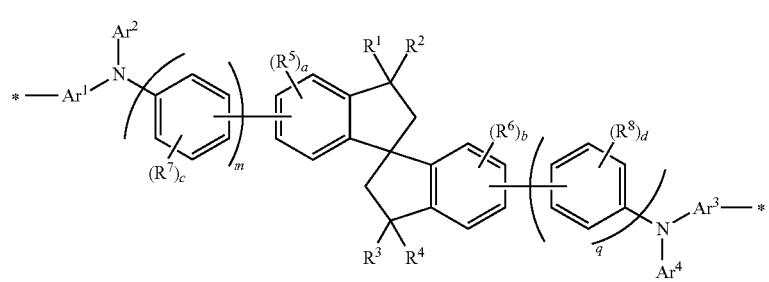

wherein:
Ar$^1$ and Ar$^3$ are the same or different and are aryl groups;
Ar$^2$ and Ar$^4$ are the same or different and are aryl groups;
R$^1$-R$^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
R$^5$-R$^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent R$^5$-R$^8$ groups can be joined together to form an aromatic ring;
a and b are the same or different and are an integer from 0-3;
c and d are the same or different at each occurrence and are an integer from 0-4;
m and q are the same or different and are an integer from 1-6; and
* represents the point of attachment in the copolymer.

All of the embodiments for Ar$^1$-Ar$^4$, R$^1$-R$^8$, a-d, m, q and n described above for Formula I, apply to Formula I-m as well.

In some embodiments, the copolymer has Formula II

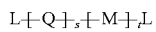  Formula II where:
L is the same or different at each occurrence and is selected from the group consisting of H, D, halogen, aryl, arylamino, crosslinkable groups, deuterated aryl, deuterated arylamino, and deuterated crosslinkable groups;
M is a conjugated moiety;
Q is a monomeric unit having Formula I-m; and
s and t represent non-zero mole fractions such that s+t=1.

In Formula II, the "Q" and "M" units can be ordered in a regular alternating pattern, in blocks of like monomers, or randomly arranged.

In some embodiments of Formula II, L is selected from aryl, arylamino, crosslinkable groups, and deuterated analogs thereof.

In some embodiments of Formula II, L is selected from phenyl, triphenylamino, and deuterated analogs thereof.

In some embodiments of Formula II, M is a deuterated aromatic moiety.

In some embodiments of Formula II, M is a monomeric unit derived from an olefin, an acetylenic compound, a stilbene, or a deuterated analog thereof.

In some embodiments of Formula II, M has Formula a, as defined above.

In some embodiments of Formula II, M has Formula b, as defined above.

In some embodiments of Formula II, group M has formula M-1

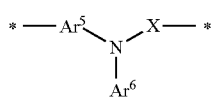

Ar$^5$ and Ar$^6$ are the same or different and are aryl groups or deuterated aryl groups;

X is the same or different at each occurrence and is selected from a single bond, an aryl group, and a deuterated aryl group; and
* indicates a point of attachment to the copolymer.

In some embodiments of formula M-1, Ar$^5$ and Ar$^6$ are selected from the group consisting of phenyl, naphthyl, anthracenyl, carbazolyl, combinations of such groups linked together covalently, and deuterated analogs thereof.

In some embodiments of formula M-1, Ar$^5$ has Formula a or Formula b, as defined above.

In some embodiments of formula M-1, Ar$^6$ has Formula c, Formula d, or Formula e, as defined above.

In some embodiments of formula M-1, X is aryl or deuterated aryl.

In some embodiments of formula M-1, X is selected from the group consisting of phenyl, naphthyl, anthracenyl, combinations of such groups linked together covalently, and deuterated analogs thereof.

In some embodiments of Formula II, group M has formula M-2:

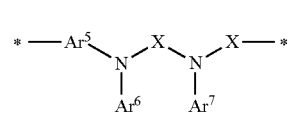

wherein:
Ar$^5$-Ar$^7$ are the same or different and are aryl groups or deuterated aryl groups;
Y is the same or different at each occurrence and is aryl, (CR'$_2$)$_q$, adamantyl, bicyclic cyclohexyl, a bicyclic group having aliphatic rings connected through a single atom, or deuterated analogs thereof;
R' is the same or different at each occurrence and is H, D, alkyl, fluoroalkyl, aryl, deuterated alkyl, deuterated fluoroalkyl, and deuterated aryl;
X is the same or different at each occurrence and is selected from a single bond, an aryl group, and a deuterated aryl group; and
* indicates a point of attachment to the copolymer.

In some embodiments of formula M-2, Ar$^3$-Ar$^5$ are selected from the group consisting of phenyl, naphthyl, anthracenyl, carbazolyl, combinations of such groups linked together covalently, and deuterated analogs thereof.

In some embodiments of formula M-2, Ar$^5$ has Formula a or Formula b, described above.

In some embodiments of formula M-2, Ar$^6$ has Formula c, Formula d, or Formula e, defined above.

In some embodiments of formula M-2, Ar$^7$ has Formula c, Formula d, or Formula e, defined above.

In some embodiments of formula M-2, X is aryl.

In some embodiments of formula M-2, X is selected from the group consisting of phenyl, naphthyl, anthracenyl, combinations of such groups linked together covalently, and deuterated analogs thereof.

In some embodiments of Formula II, group M has formula M-3

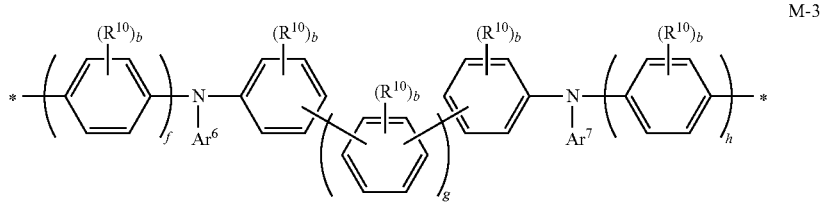

wherein:
Ar$^6$ and Ar$^7$ are the same or different and are aryl groups or deuterated aryl groups;
R$^{10}$ is independently the same or different at each occurrence and is selected from the group consisting of D, F, alkyl, aryl, alkoxy, silyl, deuterated alkyl, deuterated aryl, deuterated alkoxy, and deuterated silyl;
b is the same or different at each occurrence and is an integer from 0 to 4;
f is 1 or 2;
g is 0, 1 or 2; his 1 or 2;
h is an integer greater than 0; and
* indicates a point of attachment to the copolymer.

In some embodiments of formula M-3, Ar$^6$ and Ar$^7$ are aryl groups having no fused rings.

In some embodiments of formula M-3, Ar$^6$ has Formula c, Formula d, or Formula e, as defined above.

In some embodiments of formula M-3, Ar$^7$ has Formula c, Formula d, or Formula e, as defined above.

In some embodiments of formula M-3, Ar$^6$ and Ar$^7$ are selected from the group consisting of phenyl, biphenyl, terphenyl, deuterated analogs thereof, and derivatives thereof having one or more substituents selected from the group consisting of alkyl, alkoxy, and silyl.

In some embodiments of formula M-3, R$^{10}$ is D or C$_{1-10}$ alkyl. In some embodiments, the alkyl group is deuterated.

In some embodiments of formula M-3, all b=0.
In some embodiments of formula M-3, at least one b>0.
In some embodiments of formula M-3, f=h=2.
In some embodiments of formula M-3, g=1.
In some embodiments of formula M-3, g=2.

In some embodiments of Formula II, group M has formula M-4

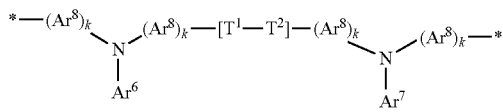

wherein:
Ar$^8$ is the same or different at each occurrence and is selected from the group consisting of phenylene, substituted phenylene, naphthylene, substituted naphthylene, and deuterated analogs thereof;
Ar$^9$ is the same or different at each occurrence and is an aryl group;
T$^1$ and T$^2$ are independently the same or different at each occurrence and are conjugated moieties which are connected in a non-planar configuration;

k is the same or different at each occurrence and is an integer from 1 to 6; and
* indicates a point of attachment to the copolymer.

In some embodiments of formula M-4, at least one Ar$^8$ is a substituted phenyl with a substituent selected from the group consisting of alkyl, alkoxy, silyl, and deuterated analogs thereof.

In some embodiments of formula M-4, k is 1-4.
In some embodiments of formula M-4, k is 1-3.
In some embodiments of formula M-4, k=1.

In some embodiments of formula M-4, Ar$^9$ has Formula c, Formula d, or Formula e, as defined above.

In some embodiments of formula M-4, Ar$^9$ is selected from the group consisting of a group having Formula a, naphthyl, phenylnaphthyl, naphthylphenyl, and deuterated analogs thereof.

In some embodiments of formula M-4, Ar$^9$ is selected from the group consisting phenyl, p-biphenyl, p-terphenyl, naphthyl, phenylnaphthyl, naphthylphenyl, and deuterated analogs thereof.

In some embodiments of formula M-4, Ar$^9$ is selected from the group consisting of phenyl, biphenyl, terphenyl, and deuterated analogs thereof.

Any of the aromatic rings in formula M-4 may be substituted at any position. The substituents may be present to improve one or more physical properties of the compound, such as solubility. In some embodiments, the substituents are selected from the group consisting of C$_{1-12}$ alkyl groups, C$_{1-12}$ alkoxy groups, silyl groups, crosslinking groups, and deuterated analogs thereof. In some embodiments, the alkyl groups are heteroalkyl groups. In some embodiments, the alkyl groups are fluoroalkyl groups.

In some embodiments of formula M-4, at least one Ar$^9$ has a substituent selected from the group consisting of alkyl, alkoxy, silyl, and deuterated analogs thereof.

In formula M-4, T$^1$ and T$^2$ are conjugated moieties. In some embodiments, T$^1$ and T$^2$ are aromatic moieties or deuterated aromatic moieties.

In some embodiments of formula M-4, T$^1$ and T$^2$ are selected from the group consisting of phenylene, napthylene, anthracenyl, and deuterated analogs thereof.

In some embodiments of formula M-4, [T$^1$-T$^2$] is a substituted biphenylene group or deuterated analog thereof. The term "biphenylene" is intended to mean a biphenyl group having two points of attachment to the compound backbone. The term "biphenyl" is intended to mean a group having two phenyl units joined by a single bond. The biphenylene group can be attached at one of the 2, 3-, 4-, or 5-positions and one of the 2', 3'-, 4'-, or 5'-positions. The substituted biphenylene group has at least one substitutent in the 2-position. In some embodiments of formula M-4, the biphenylene group has substituents in at least the 2- and 2'-positions.

In some embodiments of formula M-4, [T$^1$-T$^2$] is a binaphthylene group or deuterated binaphthylene group. The term "binaphthylene" is intended to mean a binapthyl group having 2 points of attachment to the compound backbone. The term "binaphthyl" is intended to mean a group having two naphthalene units joined by a single bond. In some embodiments, the binaphthylene group is a 1,1'-binaphthylene, which is attached to the compound backbone at one of the 3-, 4-, 5-, 6, or 7-positions and one of the 3'-, 4'-, 5'-, 6', or 7'-positions.

In some embodiments of formula M-4, [$T^1$-$T^2$] is a phenylene-naphthylene group or a deuterated phenylene-naphthylene group.

In some embodiments of formula M-4, the biphenylene, binaphthylene, and phenylene-naphthylene groups are substituted at one or more positions.

In some embodiments of formula M-4, [$T^1$-$T^2$] is a 1,1-binaphthylene group which is attached to the group backbone at the 4 and 4' positions, referred to as 4,4'-(1,1-binaphthylene).

In some embodiments of Formula II, group M has no arylamino groups.

In some embodiments of Formula II, group M has no carbazolyl groups.

In some embodiments of Formula II, group M has formula M-5

$$*—Ar^{10}—* \quad\quad M\text{-}5$$

wherein:

$Ar^{10}$ is a carbocyclic aromatic group having 6-60 ring carbons or a deuterated analog thereof; and

* indicates a point of attachment to the copolymer.

In some embodiments of formula M-5, $Ar^{10}$ is a substituted aryl group having at least one substituent selected from the group consisting of alkyl, alkoxy, silyl, crosslinking groups, and deuterated analogs thereof.

In some embodiments of formula M-5, $Ar^{10}$ is selected from the group consisting of phenyl, naphthyl, anthracenyl, combinations of such groups linked together covalently, substituted derivatives thereof, and deuterated analogs thereof.

In some embodiments of formula M-5, $Ar^{10}$ is selected from the group consisting of phenyl, biphenyl, terphenyl, substituted derivatives thereof, and deuterated analogs thereof.

In some embodiments of Formula II, s>t.

In some embodiments of Formula II, s is in the range of 0.5-0.99; in some embodiments, 0.6-0.95; in some embodiments, 0.75-0.95.

Any of the above embodiments for Formula II can be combined with one or more of the other embodiments, so long as they are not mutually exclusive. For example, the embodiment in which $Ar^1$=$Ar^3$ can be combined with the embodiment in which M has formula M-1. The same is true for the other non-mutually-exclusive embodiments discussed above. The skilled person would understand which embodiments were mutually exclusive and would thus readily be able to determine the combinations of embodiments that are contemplated by the present application.

The copolymer having Formula II can be made using known coupling techniques and polymerization techniques.

Some non-limiting examples of copolymers having Formula II are shown below.

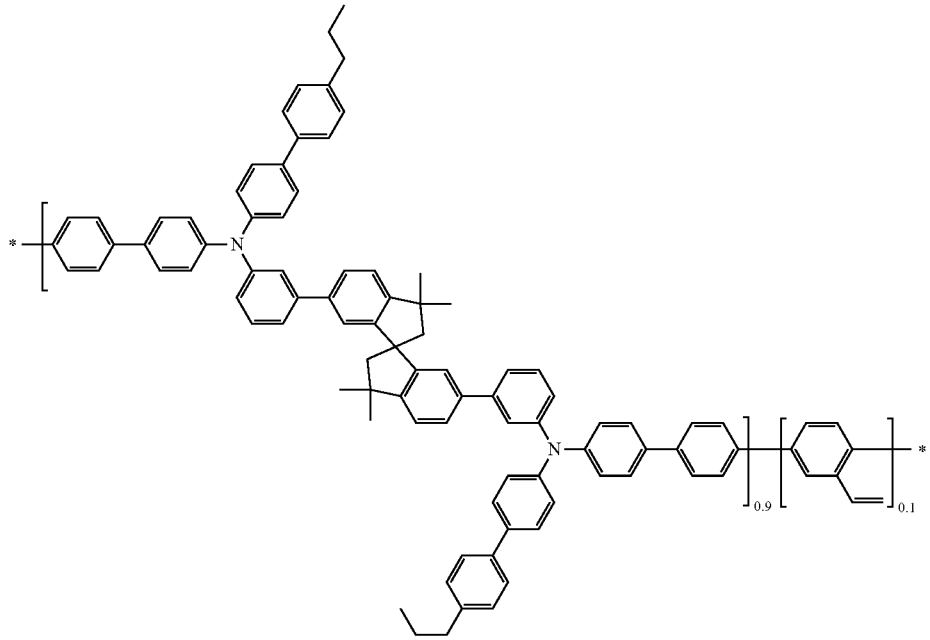

Compound H17

Compound H18

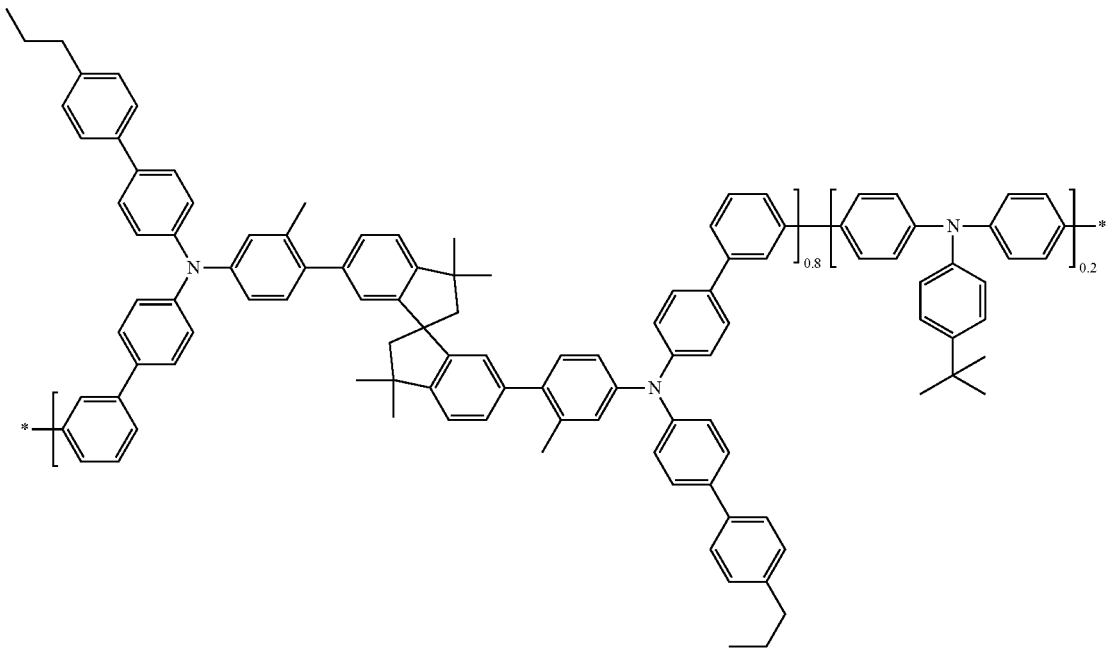

In the above compounds, the * indicates a point of attachment to the copolymer.

4. Electronic Devices

Organic electronic devices that may benefit from having one or more layers including at least one compound as described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), (4) devices that convert light of one wavelength to light of a longer wavelength, (e.g., a down-converting phosphor device); and (5) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure is shown in FIG. 1. The device 100 has a first electrical contact layer, an anode layer 110 and a second electrical contact layer, a cathode layer 160, and a photoactive layer 140 between them. Additional layers may optionally be present. Adjacent to the anode may be a hole injection layer 120, sometimes referred to as a buffer layer. Adjacent to the hole injection layer may be a hole transport layer 130, including hole transport material. Adjacent to the cathode may be an electron transport layer 150, including an electron transport material. As an option, devices may use one or more additional hole injection or hole transport layers (not shown) next to the anode 110 and/or one or more additional electron injection or electron transport layers (not shown) next to the cathode 160. Layers 120 through 150 are individually and collectively referred to as the organic active layers.

Figure 2:
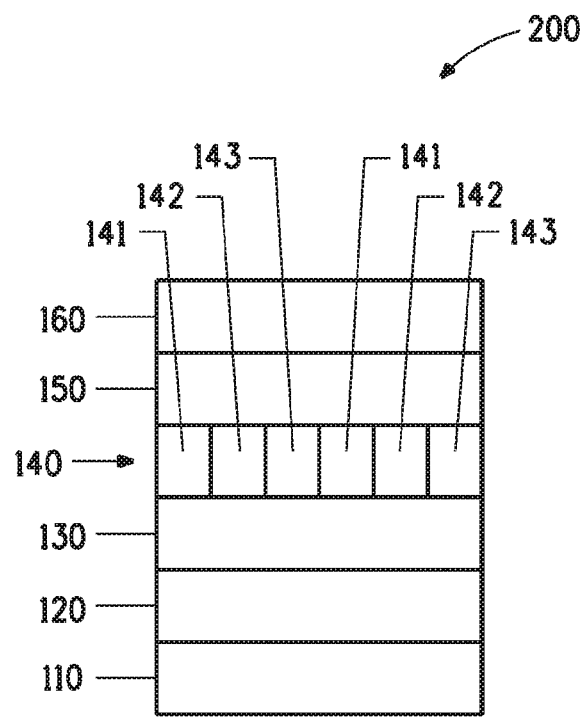
FIG. 2 includes an illustration of another example of an organic electronic device.

In some embodiments, in order to achieve full color, the light-emitting layer is pixellated, with subpixel units for each of the different colors. An illustration of a pixellated device is shown in FIG. 2. The device 200 has anode 110, hole injection layer 120, hole transport layer 130, electroluminescent layer 140, electron transport layer 150, and cathode 160. The electroluminescent layer is divided into subpixels 141, 142, 143, which are repeated across the layer. In some embodiments, the subpixels represent red, blue and green color emission. Although three different subpixel units are depicted in FIG. 2, two or more than three subpixel units may be used.

The different layers will be discussed further herein with reference to FIG. 1. However, the discussion applies to FIG. 2 and other configurations as well.

In some embodiments, the different layers have the following range of thicknesses: anode 110, 500-5000 Å, in some embodiments, 1000-2000 Å; hole injection layer 120, 50-2000 Å, in some embodiments, 200-1000 Å; hole transport layer 130, 50-3000 Å, in some embodiments, 200-2000 Å; photoactive layer 140, 10-2000 Å, in some embodiments, 100-1000 Å; electron transport layer 150, 50-2000 Å, in some embodiments, 100-1000 Å; cathode 160, 200-10000 Å, in some embodiments, 300-5000 Å. The desired ratio of layer thicknesses will depend on the exact nature of the materials used.

One or more of the new compounds having Formula I or Formula II described herein may be present in one or more of the electroactive layers of a device. In some embodiments, the new compounds are useful as hole transport materials in layer 130. In some embodiments, the new compounds are useful as host materials for photoactive dopant materials in photoactive layer 140. The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material. The term "host material" is intended to mean a material to which a dopant is added. The host material may or may not have electronic characteristic(s) or the ability to emit, receive, or filter radiation. In some embodiments, the host material is present in higher concentration.

In some embodiments, an organic electronic device includes an anode, a cathode, and at least one organic active layer therebetween, where the organic active layer includes a compound of Formula I.

In some embodiments, an organic electronic device includes an anode, a cathode, and a photoactive layer therebetween, and further includes an additional organic active layer including a compound of Formula I. In some embodiments, the additional organic active layer is a hole transport layer.

In some embodiments, an organic electronic device includes an anode, a cathode, and at least one organic active layer therebetween, where the organic active layer includes a compound of Formula II.

In some embodiments, an organic electronic device includes an anode, a cathode, and a photoactive layer therebetween, and further includes an additional organic active layer including a compound of Formula II. In some embodiments, the additional organic active layer is a hole transport layer.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also include an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

Optional hole injection layer 120 includes hole injection materials. The term "hole injection layer" or "hole injection material" is intended to mean electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules, and may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The hole injection layer 120 can include charge transfer compounds, and the like, such as copper phthalocyanine and the tetrathiafulvalene-tetracyanoquinodimethane system (TTF-TCNQ). In some embodiments, the hole injection layer 120 is made from a dispersion of a conducting polymer and a colloid-forming polymeric acid. Such materials have been described in, for example, published U.S. patent applications 2004-0102577, 2004-0127637, and 2005-0205860.

Layer 130 includes hole transport material. In some embodiments, the hole transport layer includes a compound having Formula I or Formula II.

In some embodiments, the hole transport layer includes only a compound having Formula I, where additional materials that would materially alter the principle of operation or the distinguishing characteristics of the layer are not present therein.

In some embodiments, the hole transport layer includes only a compound having Formula II, where additional materials that would materially alter the principle of operation or the distinguishing characteristics of the layer are not present therein.

In some embodiments, layer 130 includes other hole transport material. Examples of hole transport materials for the hole transport layer have been summarized for example, in Kirk-Othmer Encyclopedia of Chemical Technology, Fourth Edition, Vol. 18, p. 837-860, 1996, by Y. Wang. Both hole transporting small molecules and polymers can be used. Commonly used hole transporting molecules include, but are not limited to: 4,4',4"-tris(N,N-diphenyl-amino)-triphenylamine (TDATA); 4,4',4"-tris(N-3-methylphenyl-N-phenyl-amino)-triphenylamine (MTDATA); N,N'-diphenyl-N, N'-bis(3-methylphenyl)-[1,1'-biphenyl]-4,4'-diamine (TPD); 4, 4'-bis(carbazol-9-yl)biphenyl (CBP); 1,3-bis(carbazol-9-yl)benzene (mCP); 1,1-bis[(di-4-tolylamino) phenyl]cyclohexane (TAPC); N,N'-bis(4-methylphenyl)-N, N-bis(4-ethylphenyl)-[1,1'-(3,3'-dimethyl)biphenyl]-4,4'-diamine (ETPD); tetrakis-(3-methylphenyl)-N, N, N',N'-2,5-phenylenediamine (PDA); α-phenyl-4-N,N-diphenylaminostyrene (TPS); p-(diethylamino)benzaldehyde diphenylhydrazone (DEH); triphenylamine (TPA); bis[4-(N, N-diethylamino)-2-methylphenyl](4-methylphenyl)methane (MPMP); 1-phenyl-3[p-(diethylamino)styryl]-5-[p-(diethylamino)phenyl]pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); N,N'-bis(naphthalen-1-yl)-N,N'-bis-(phenyl)benzidine (α-NPB); and porphyrinic compounds, such as copper phthalocyanine. Commonly used hole transporting polymers include, but are not limited to, polyvinylcarbazole, (phenylmethyl)polysilane, poly(dioxythiophenes), polyanilines, and polypyrroles. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9, 10-dianhydride.

Depending upon the application of the device, the photoactive layer 140 can be a light-emitting layer that is activated by an applied voltage (such as in a light-emitting diode or light-emitting electrochemical cell), a layer of material that absorbs light and emits light having a longer wavelength (such as in a down-converting phosphor device), or a layer of material that responds to radiant energy and generates a signal with or without an applied bias voltage (such as in a photodetector or photovoltaic device).

In some embodiments, the photoactive layer includes an organic electroluminescent ("EL") material. Any EL material can be used in the devices, including, but not limited to, small molecule organic fluorescent compounds, fluorescent and phosphorescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. In some cases the small molecule fluorescent or organometallic materials are deposited as a dopant with a host material to improve processing and/or electronic properties. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In some embodiments, photoactive layer 140 includes an electroluminescent material in a host material having Formula I. In some embodiments, a second host material is also present. In some embodiments, photoactive layer 140 includes only an electroluminescent material and a host material having Formula I. In some embodiment, photoactive layer 140 includes only an electroluminescent material, a first host material having Formula I, and a second host material. Examples of second host materials include, but are not limited to, chrysenes, phenanthrenes, triphenylenes, phenanthrolines, naphthalenes, anthracenes, quinolines, isoquinolines, quinoxalines, phenylpyridines, benzodifurans, and metal quinolinate complexes.

In some embodiments, photoactive layer 140 includes an electroluminescent material in a host material having Formula II. In some embodiments, a second host material is also present. In some embodiments, photoactive layer 140 includes only an electroluminescent material and a host material having Formula II. In some embodiment, photoactive layer 140 includes only an electroluminescent material, a first host material having Formula II, and a second host material. Examples of second host materials include, but are not limited to, chrysenes, phenanthrenes, triphenylenes, phenanthrolines, naphthalenes, anthracenes, quinolines, isoquinolines, quinoxalines, phenylpyridines, benzodifurans, and metal quinolinate complexes.

Optional layer 150 can function both to facilitate electron transport, and also serve as a hole injection layer or confinement layer to prevent quenching of the exciton at layer interfaces. Preferably, this layer promotes electron mobility and reduces exciton quenching. Examples of electron transport materials which can be used in the optional electron transport layer 150, include metal chelated oxinoid compounds, including metal quinolate derivatives such as tris (8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole) benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); triazines; fullerenes; and mixtures thereof. In some embodiments, the electron transport material is selected from the group consisting of metal quinolates and phenanthroline derivatives. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

An optional electron injection layer may be deposited over the electron transport layer. Examples of electron injection materials include, but are not limited to, Li-containing organometallic compounds, LiF, $Li_2O$, Li quinolate, Cs-containing organometallic compounds, CsF, $Cs_2O$, and $Cs_2CO_3$. This layer may react with the underlying electron transport layer, the overlying cathode, or both. When an electron injection layer is present, the amount of material deposited is generally in the range of 1-100 Å, in some embodiments 1-10 Å.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device layers can be formed by any deposition technique, or combinations of techniques, including vapor deposition, liquid deposition, and thermal transfer. Substrates such as glass, plastics, and metals can be used. Conventional vapor deposition techniques can be used, such as thermal evaporation, chemical vapor deposition, and the like. The organic layers can be applied from solutions or dispersions in suitable solvents, using conventional coating or printing techniques, including but not limited to spin-coating, dip-coating, roll-to-roll techniques, ink-jet printing, continuous nozzle printing, screen-printing, gravure printing and the like.

For liquid deposition methods, a suitable solvent for a particular compound or related class of compounds can be readily determined by one skilled in the art. For some applications, it is desirable that the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics such as toluene, xylenes, trifluorotoluene and the like. Other suitable liquids for use in making the liquid composition, either as a solution or dispersion as described herein, including the new compounds, includes, but not limited to, chlorinated hydrocarbons (such as methylene chloride, chloroform, chlorobenzene), aromatic hydrocarbons (such as substituted and non-substituted toluenes and xylenes), including triflurotoluene), polar solvents (such as tetrahydrofuran (THP), N-methyl pyrrolidone) esters (such as ethylacetate) alcohols (isopropanol), ketones (cyclopentatone) and mixtures thereof. Suitable solvents for electroluminescent materials have been described in, for example, published PCT application WO 2007/145979.

In some embodiments, the device is fabricated by liquid deposition of the hole injection layer, the hole transport layer, and the photoactive layer, and by vapor deposition of the anode, the electron transport layer, an electron injection layer and the cathode.

It is understood that the efficiency of devices made with the new compositions described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

In some embodiments, the device has the following structure, in order: anode, hole injection layer, hole transport layer, photoactive layer, electron transport layer, electron injection layer, cathode.

Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Synthesis Example 1

This example illustrates the preparation of intermediate compounds.

a) Synthesis of Compound 2

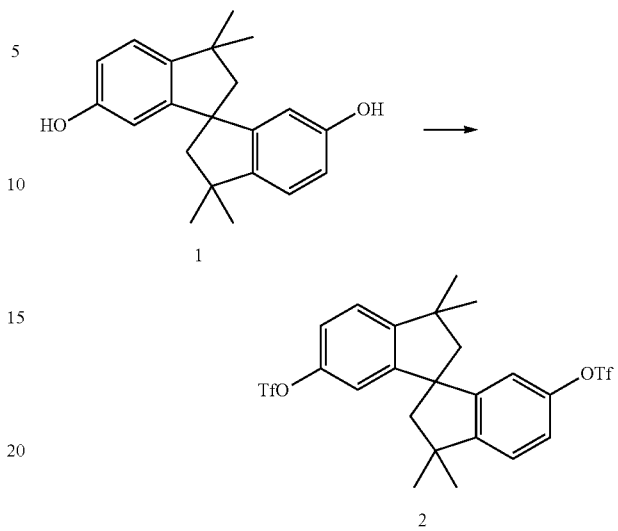

Spiro-bisphenol 1 was synthesized following the procedure reported by Chen, W.-F.; Lin, H.-Y.; Dai, S. A. Org. Letters 2004, 6, 2341.

Diol 1 (10.0 g, 32.4 mmol) was dissolved in 300 mL of dichloromethane and cooled to 0 C. Triflic anhydride (13.1 mL, 77.8 mmol) was slowly added and the reaction was allowed to slowly warm up to room temperature overnight. The resulting mixture was quenched with 0.5 M HCl. The layers were separated and the organic layer was washed with a sodium carbonate solution, water and then brine. Evaporation of the volatiles yielded a light pink solid in 81% yield (15 g).

b) Synthesis of Compound 3

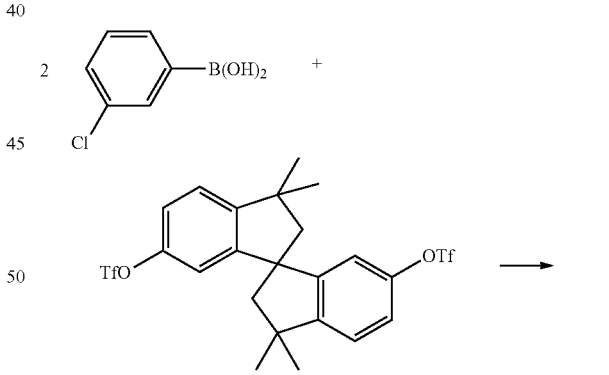

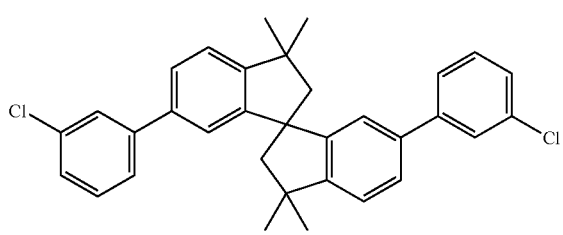

Under an atmosphere of nitrogen a round bottom flask was charged with ditriflate 2 (4.40 g, 7.7 mmol), 3-chloro phenyl boronic acid (2.64 g, 16.9 mmol), cesium carbonate (15.02 g, 46.11 mmol) and dimethoxyethane (30 mL), water (5 mL) and ethanol (15 mL). The resulting mixture was degassed for 20 minutes after which 1,1'-bis(diphenylphosphino)ferrocene]dichloropalladium(II) (0.253 g, 0.346 mmol) was added and the solution was further degassed for 5 minutes. The mixture was heated 19 hours at 55° C. After cooling, water (100 mL) and dichloromethane were added to the reaction mixture and the contents were transferred to a separatory funnel. The organic layer was washed with saturated sodium bicarbonate followed by brine. The organic layer was filtered through a silica plug and the filtrate was rotary evaporated to give a crude pink solid (17 g). The solution was dissolved in DCM, dried on Celite and purified using chromatography (100% hexane). The material was concentrated and collected via filtration from a slurry in hexanes to give a white solid in 57% yield (2.19 g).

c) Synthesis of Compound 4

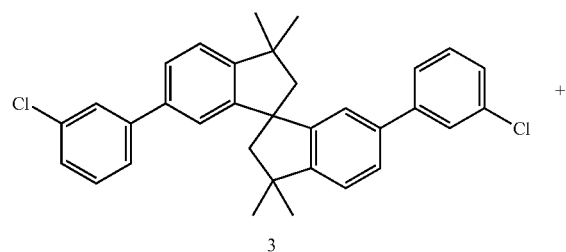

3

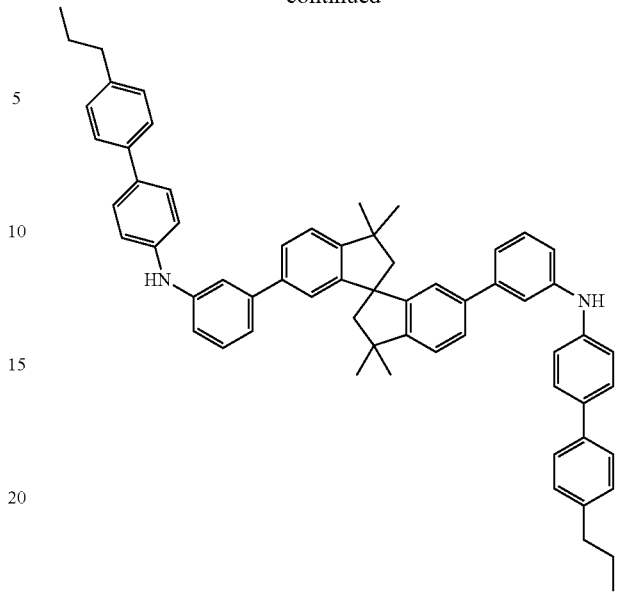

4

Under an atmosphere of nitrogen a vial was charged with compound 3 (1.00 g, 2.01 mmol), 4-propylaminobiphenyl (2.02 g, 4.42 mmol), Pd$_2$(dba)$_3$ (0.092 g, 0.1 mmol), tri-t-butylphosphine (0.092 g, 0.2 mmol) and toluene (22 mL). The resulting solution was stirred for 10 minutes followed by addition of NaO$^t$Bu (0.48 g, 5.03 mmol). The reaction was stirred at room temperature overnight followed by heating to 90° C. for 18 hrs. After cooling to room temperature, the resulting thick solution was diluted with toluene (~100 mL) and filtered through a silica pad. Evaporation of the volatiles and purification on silica using a mixture of dicholoromethane/hexane as the eluent yielded compound 4 in 59% yield (1.00 g).

d) Synthesis of Compound 5

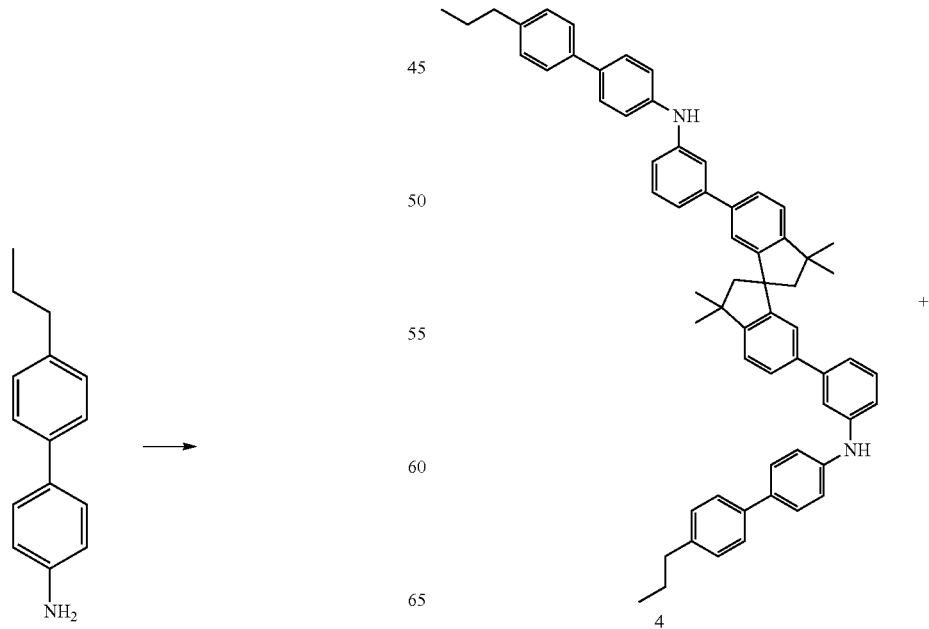

4

-continued

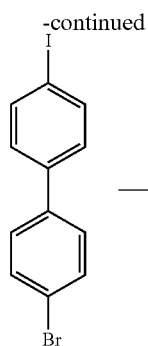

5

Under an atmosphere of nitrogen a vial was charged with diamine 4 (1.00 g, 1.18 mmol), 4,4'-iodobromobiphenyl (1.27 g, 3.54 mmol), $Pd_2(dba)_3$ (0.086 g, 0.094 mmol), 1,1'-bis(diphenylphosphino)ferrocene (0.0105 g, 0.19 mmol) and toluene (40 mL). The resulting solution was stirred for 10 minutes followed by addition of NaO$^t$Bu (0.284 g, 2.95 mmol). The reaction was heated to 90° C. for 22 hrs. After cooling to room temperature, the resulting thick solution was diluted with toluene (~100 mL) and filtered through a silica pad. Evaporation of the volatiles and purification on silica using a mixture of dicholoromethane and hexane (0-40%) as the eluent yielded compound 5 in 65% yield (1.00 g).

e) Synthesis of Compound 6-8

These monomers were synthesized as exemplified in the syntheses of compounds 1-5.

compound 6
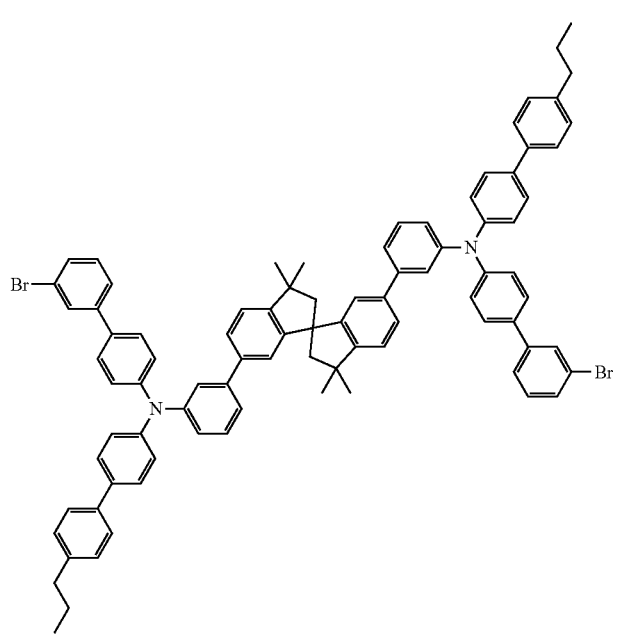
compound 7
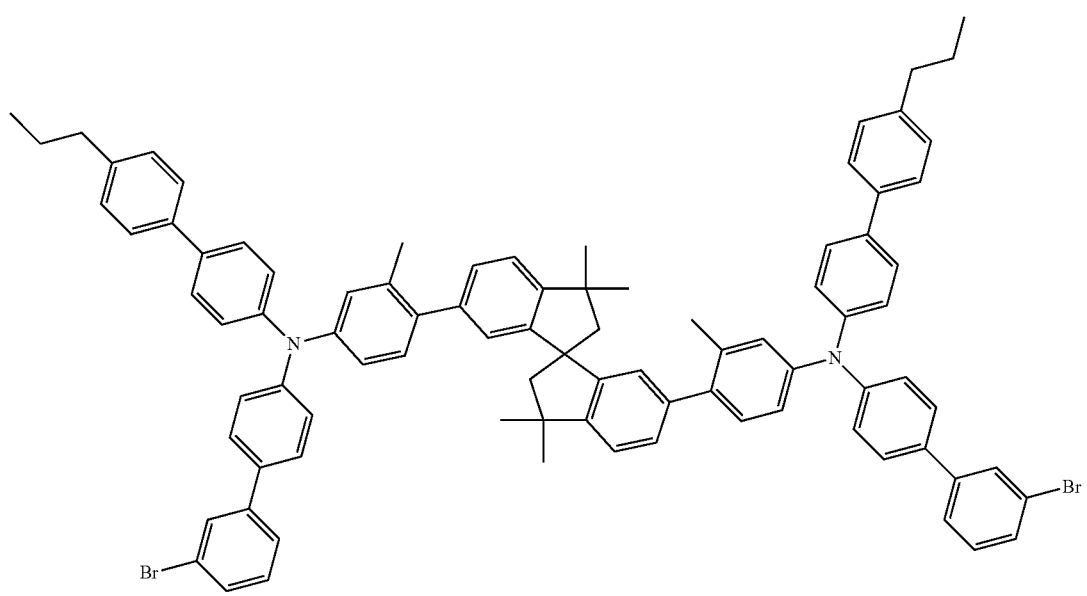

-continued
compound 8
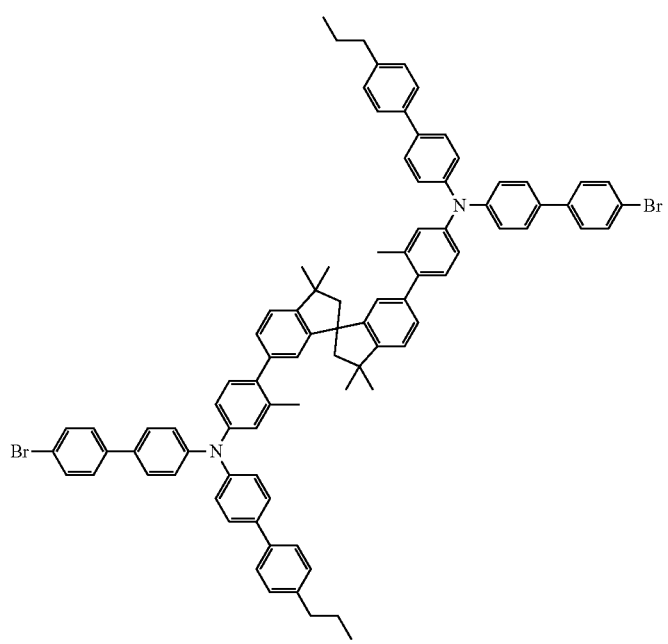
Synthesis Example 2
This example illustrates the preparation of Compound H11.
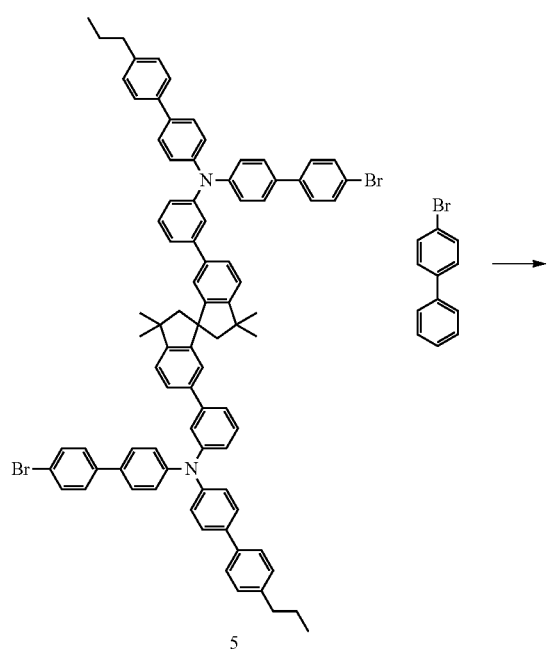
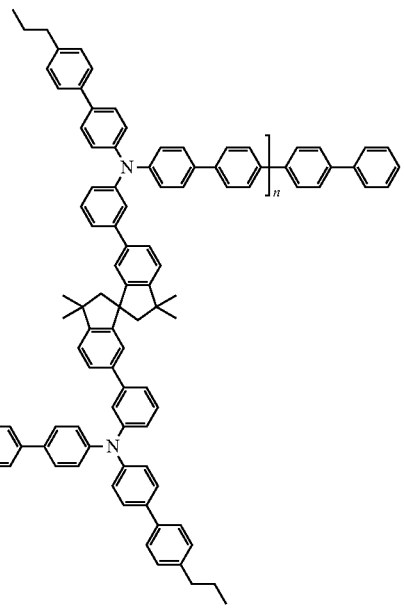
H11
Compound 5 (0.459 mmol) and 4-bromobiphenyl (0.007 mmol) were added to a scintillation vial and dissolved in 15 mL toluene. A clean, dry 50 mL Schlenk tube was charged with bis(1,5-cyclooctadiene)nickel(0) (0.941 mmol). 2,2'-Dipyridyl (0.941 mmol) and 1,5-cyclooctadiene (0.941 mmol) were weighed into a scintillation vial and dissolved in 3.75 mL N,N'-dimethylformamide. The solution was added to the Schlenk tube, which was then inserted into an aluminum block and heated to an internal temperature of 60° C. The catalyst system was held at 60° C. for 30 minutes. The monomer solution in toluene was added to the Schlenk tube and the tube was sealed. The polymerization mixture was stirred at 60° C. for three hours. The Schlenk tube was then removed from the block and allowed to cool to room temperature. The contents were poured into HCl/methanol (5% v/v, conc. HCl). After stirring for 45 minutes, the polymer was collected by vacuum filtration and dried under high vacuum. The polymer was dissolved in toluene (1% wt/v) and passed through a column containing aluminum oxide, basic. (6 gram) layered onto silica gel (6 gram). The polymer/toluene filtrate was concentrated (3% wt/v toluene) and triturated with 3-pentanone. The toluene/3-pentanone solution was decanted from the semi-solid polymer which was then dissolved with 10 mL toluene before being poured into stirring methanol to yield compound H11 in 24% yield. GPC analysis with polystyrene standards Mn=49,373; Mw=112,210; PDI=2.3.

Synthesis Example 3

This example illustrates the preparation of Compound H12.

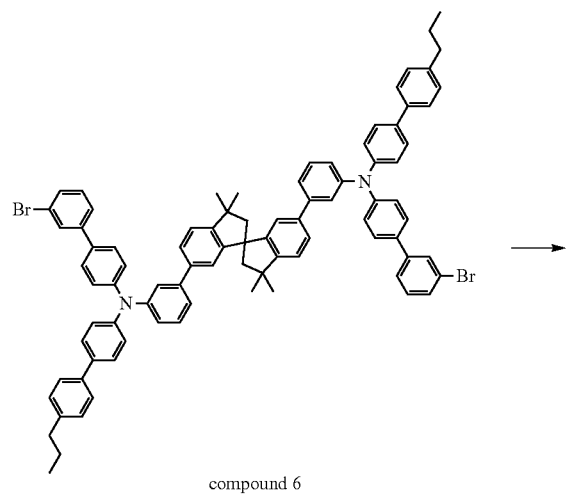

compound 6

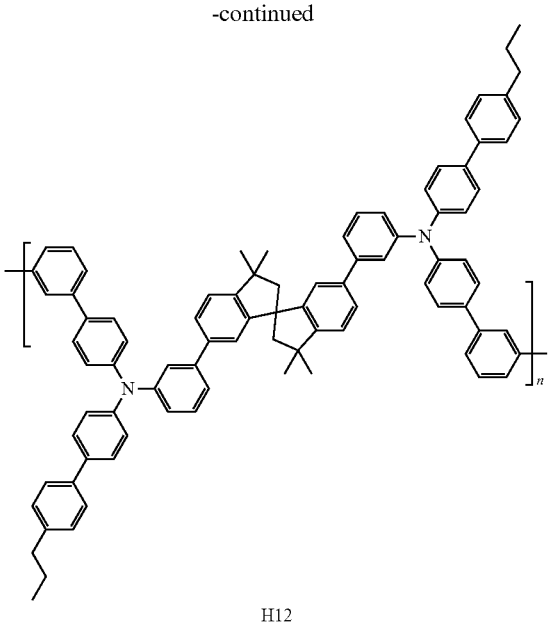

H12

Compound 6 (0.466 mmol) was added to a scintillation vial and dissolved in 15 mL toluene. A clean, dry 50 mL Schlenk tube was charged with bis(1,5-cyclooctadiene)nickel(0) (0.941 mmol). 2,2'-Dipyridyl (0.941 mmol) and 1,5-cyclooctadiene (0.941 mmol) were weighed into a scintillation vial and dissolved in 3.75 mL N,N'-dimethylformamide. The solution was added to the Schlenk tube, which was then inserted into an aluminum block and heated to an internal temperature of 60° C. The catalyst system was held at 60° C. for 30 minutes. The monomer solution in toluene was added to the Schlenk tube and the tube was sealed. The polymerization mixture was stirred at 60° C. for three hours. The Schlenk tube was then removed from the block and allowed to cool to room temperature. The contents were poured into HCl/methanol (5% v/v, conc. HCl). After stirring for 45 minutes, the polymer was collected by vacuum filtration and dried under high vacuum. The polymer was dissolved in toluene (1% wt/v) and passed through a column containing aluminum oxide, basic (6 gram) layered onto silica gel (6 gram). The polymer/toluene filtrate was concentrated (2.5% wt/v toluene) and poured into stirring methanol to yield compound H12 in 78% yield. GPC analysis with polystyrene standards Mn=10,247; Mw=42,098; PDI=4.1.

Synthesis Example 4

This example illustrates the preparation of Compound H14.

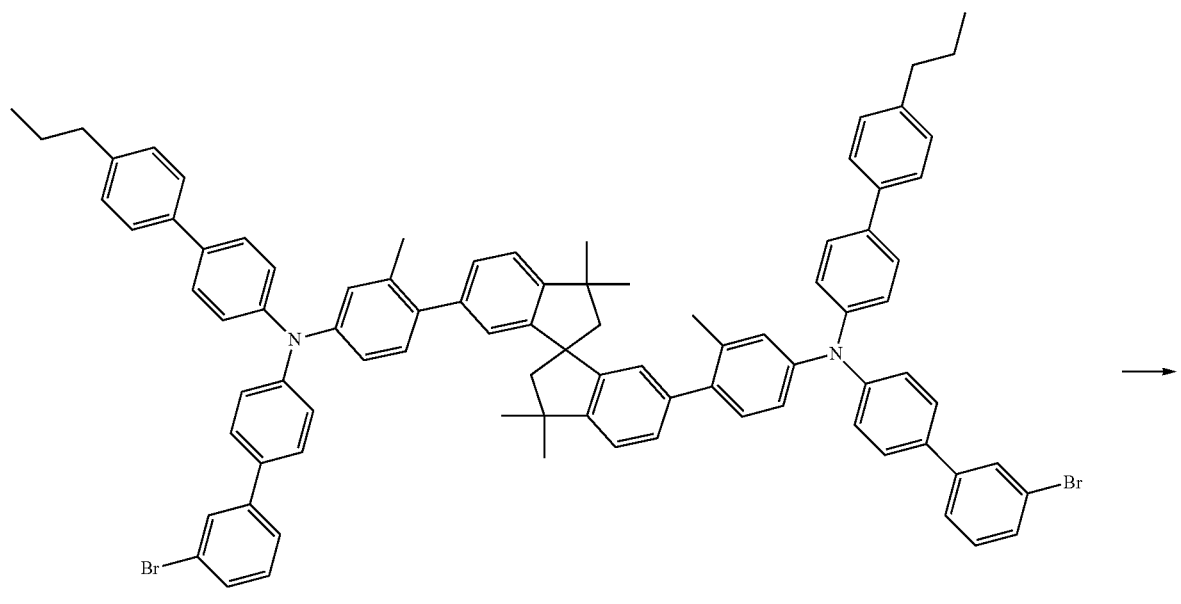

compound 7

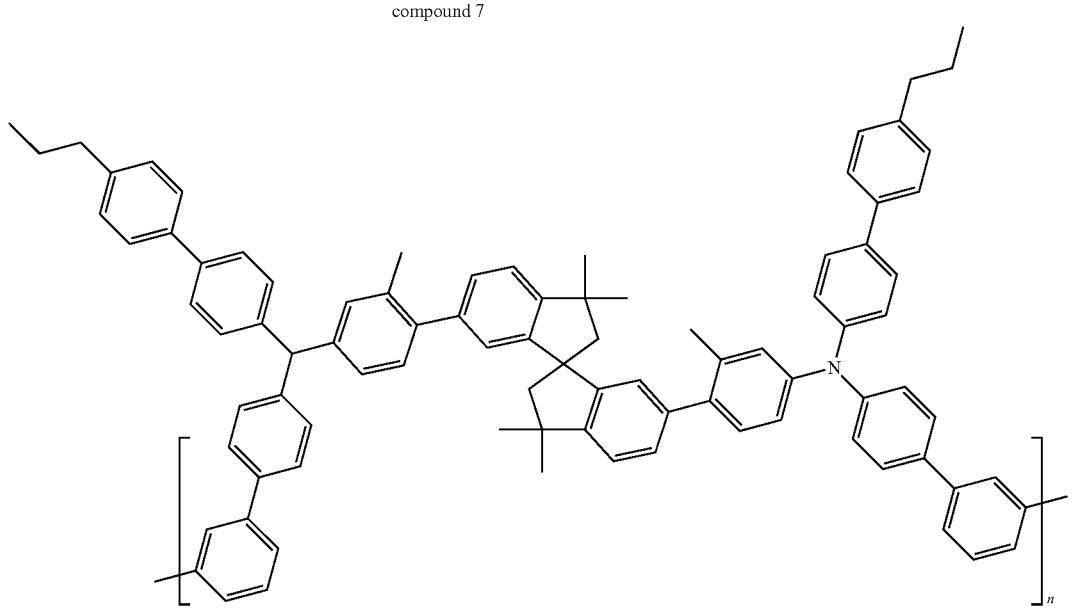

H14

Compound 7 (0.374 mmol) was added to a scintillation vial and dissolved in 12 mL toluene. A clean, dry 50 mL Schlenk tube was charged with bis(1,5-cyclooctadiene)nickel(0) (0.755 mmol). 2,2'-Dipyridyl (0.755 mmol) and 1,5-cyclooctadiene (0.755 mmol) were weighed into a scintillation vial and dissolved in 3.14 mL N,N'-dimethylformamide. The solution was added to the Schlenk tube, which was then inserted into an aluminum block and heated to an internal temperature of 60° C. The catalyst system was held at 60° C. for 30 minutes. The monomer solution in toluene was added to the Schlenk tube and the tube was sealed. The polymerization mixture was stirred at 60° C. for three hours. The Schlenk tube was then removed from the block and allowed to cool to room temperature. The contents were poured into HCl/methanol (5% v/v, conc. HCl). After stirring for 45 minutes, the polymer was collected by vacuum filtration and dried under high vacuum. The polymer was dissolved in toluene (1% wt/v) and passed through a column containing aluminum oxide, basic (6 gram) layered onto silica gel (6 gram). The polymer/toluene filtrate was concentrated (2.5% wt/v toluene) and triturated with 3-pentanone. The toluene/3-pentanone solution was decanted from the semi-solid polymer which was then dissolved with 6 mL toluene before being poured into stirring methanol to yield compound H14 in 15% yield. GPC analysis with polystyrene standards Mn=5,505; Mw=21,918; PDI=4.0

Synthesis Example 5

This example illustrates the preparation of Compound H13.

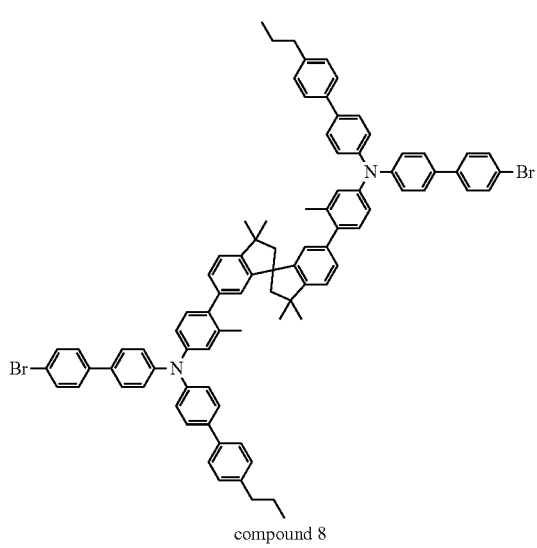

compound 8

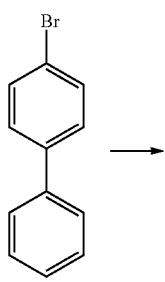

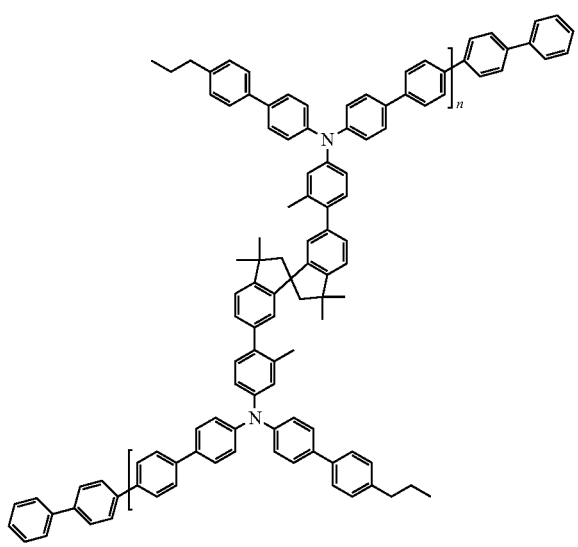

H13

Compound 8 (0.449 mmol) and 4-bromobiphenyl (0.021 mmol) were added to a scintillation vial and dissolved in 15 mL toluene. A clean, dry 50 mL Schlenk tube was charged with bis(1,5-cyclooctadiene)nickel(0) (0.949 mmol). 2,2'-Dipyridyl (0.949 mmol) and 1,5-cyclooctadiene (0.949 mmol) were weighed into a scintillation vial and dissolved in 3.75 mL N,N'-dimethylformamide. The solution was added to the Schlenk tube, which was then inserted into an aluminum block and heated to an internal temperature of 60° C. The catalyst system was held at 60° C. for 30 minutes. The monomer solution in toluene was added to the Schlenk tube and the tube was sealed. The polymerization mixture was stirred at 60° C. for three hours. The Schlenk tube was then removed from the block and allowed to cool to room temperature. The contents were poured into HCl/methanol (5% v/v, conc. HCl). After stirring for 45 minutes, the polymer was collected by vacuum filtration and dried under high vacuum. The polymer was dissolved in toluene (1% wt/v) and passed through a column containing aluminum oxide, basic. (10 gram) layered onto silica gel (10 gram). The polymer/toluene filtrate was concentrated (2.5% wt/v toluene) and triturated with 3-pentanone. The toluene/3-pentanone solution was decanted from the semi-solid polymer which was then dissolved with 5 mL toluene before being poured into stirring methanol to yield compound H13 in 18% yield. GPC analysis with polystyrene standards Mn=21,345; Mw=46,137; PDI=2.2.

Device Examples

These examples demonstrate the fabrication and performance of OLED devices.

(1) Materials

HIJ-1 is an electrically conductive polymer doped with a polymeric fluorinated sulfonic acid.

HT-A is the triarylamine polymer shown below

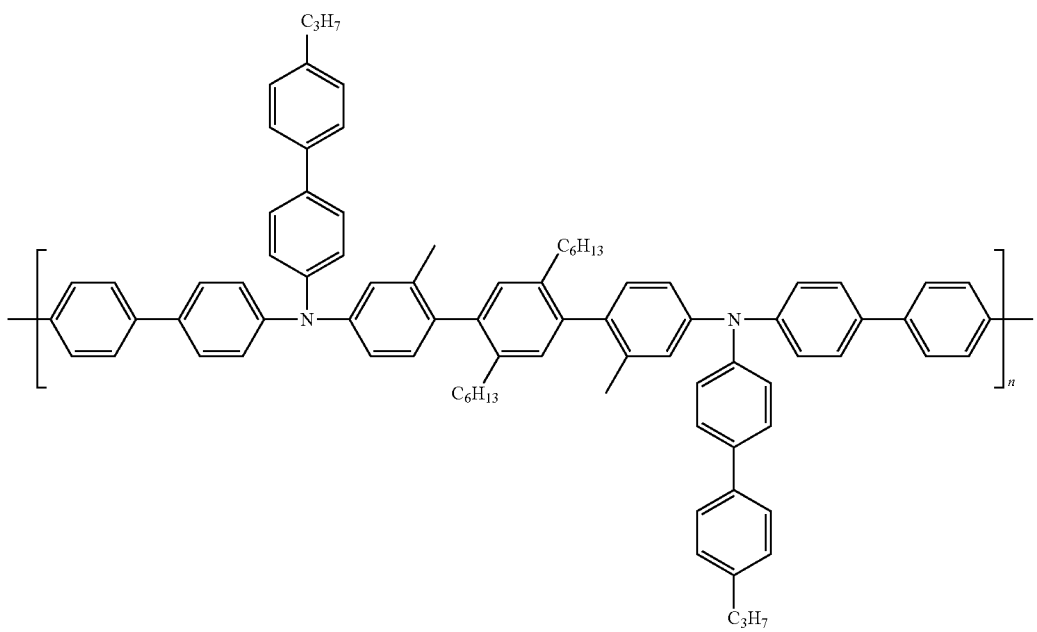

Host-1 is a deuterated 9,10-diarylanthracene compound.
Dopant-1 is a bis(diarylamino)benzofluorene compound.
Dopant-2 is bis(diarylamino)chrysene compound.
ET-1 is a triarylfluoranthene
EIJ-1 is a quinolate compound.

The devices had the following structure on a glass substrate:
  Compound anode=ITO (50 nm)
  hole injection layer=HIJ-1 (100 nm)
  hole transport layer=shown below
  photoactive layer=shown below
  electron transport layer=ET-1 (20 nm)
  electron injection layer/cathode=EIJ-1/Al (3/100 nm)

(2) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission.

The patterned ITO substrates were cleaned and spin-coated with an aqueous dispersion of HIJ-1 and heated to dry. The hole transport layer was formed by spin-coating from solvent solution and heated to dry.

In some examples, after formation of the hole transport layer, the workpieces were then spin-coated with a solution of the photoactive layer materials in methyl benzoate and heated to remove solvent. The workpieces were then masked and place in a vacuum chamber. A layer of ET-1 was deposited by thermal evaporation, followed by a layer of EIJ-1. Masks were then changed in vacuo and a layer of Al was deposited by thermal evaporation. The chamber was vented, and the devices were encapsulated using a glass lid, desiccant, and UV curable epoxy.

In some examples, after formation of the hole transport layer, the workpieces were masked and placed in a vacuum chamber. The materials in the photoactive layer were then deposited by thermal evaporation. A layer of ET-1 was then deposited by thermal evaporation, followed by a layer of EIJ-1. Masks were then changed in vacuo and a layer of Al was deposited by thermal evaporation. The chamber was vented, and the devices were encapsulated using a glass lid, desiccant, and UV curable epoxy.

(3) Device Characterization

The OLED samples were characterized by measuring their (1) current-voltage (I-V) curves, (2) electroluminescence luminance versus voltage, and (3) electroluminescence spectra versus voltage. All three measurements were performed at the same time and controlled by a computer. The current efficiency of the device at a certain voltage is determined by dividing the electroluminescence luminance of the LED by the current density needed to run the device. The unit is a cd/A. The color coordinates were determined using either a Minolta CS-100 meter or a Photoresearch PR-705 meter.

Example 1 and Comparative Example A

This example illustrates the use of a compound having Formula I as hole transport material in a device, where the photoactive layer is made by solution deposition.

In Example 1, the hole transport layer was Compound H11, with a final thickness of 72 nm.

In Comparative Example A, the hole transport layer was compound HT-A, with a final thickness of 94 nm.

The photoactive layer contained Host-1 and Dopant-1 in a weight ratio of 93:7, with a final thickness of 40 nm.

The results are given in Table 1.

TABLE 1

Device results

| Ex. | HTL | Voltage @ 20 mA/cm2 (V) | EQE (%) | CE (cd/A) | P.E. (lm/W) | CIE (x, y) |
|---|---|---|---|---|---|---|
| 1 | H11 | 3.9 | 2.4 | 3.8 | 2.8 | 0.147 0.223 |
| Comp. A | HT-A | 5.1 | 5.5 | 4.3 | 2.5 | 0.145 0.083 |

All data @ 1000 nits. HTL is the hole transport layer; EQE is the external quantum efficiency; CE is the current efficiency; P.E. is the power efficiency; CIE(x,y) are the x and y color coordinates according to the C.I.E. chromaticity scale (Commission Internationale de L'Eclairage, 1931).

Example 2 and Comparative Example B

This example illustrates the use of a compound having Formula I as hole transport material in a device, where the photoactive layer is made by vapor deposition.

In Example 2, the hole transport layer was Compound H11, with a final thickness of 72 nm.

In Comparative Example B, the hole transport layer was compound HT-A, with a final thickness of 94 nm.

The photoactive layer contained Host-1 and Dopant-2 in a weight ratio of 6:1, with a final thickness of 38 nm.

The results are given in Table 2.

TABLE 2

Device results

| Ex. | HTL | Voltage @ 20 mA/cm2 (V) | EQE (%) | CE (cd/A) | P.E. (lm/W) | CIE (x, y) |
|---|---|---|---|---|---|---|
| 2 | H11 | 4.6 | 5.3 | 5.2 | 3.5 | 0.146 0.111 |
| Comp. B | HT-A | 4.6 | 8.4 | 7.3 | 5.0 | 0.141 0.097 |

All data @ 1000 nits. HTL is the hole transport layer; EQE is the external quantum efficiency; CE is the current efficiency; P.E. is the power efficiency; CIE(x,y) are the x and y color coordinates according to the C.I.E. chromaticity scale (Commission Internationale de L'Eclairage, 1931).

Example 3 and Comparative Example C

This example illustrates the use of a compound having Formula I as hole transport material in a device, where the photoactive layer is made by vapor deposition.

In Example 3, the hole transport layer was Compound H14, with a final thickness of 100 nm.

In Comparative Example C, the hole transport layer was compound HT-A, with a final thickness of 100 nm.

The photoactive layer contained Host-1 and Dopant-2 in a weight ratio of 6:1, with a final thickness of 38 nm.

The results are given in Table 3.

TABLE 3

Device results

| Ex. | HTL | Voltage @ 20 mA/cm2 (V) | EQE (%) | CE (cd/A) | P.E. (lm/W) | CIE (x, y) |
|---|---|---|---|---|---|---|
| 3 | H14 | 5.0 | 9.0 | 8.1 | 5.3 | 0.139 0.103 |
| Comp. C | HT-A | 4.2 | 8.7 | 8.2 | 6.1 | 0.136 0.111 |

All data @ 1000 nits. HTL is the hole transport layer; EQE is the external quantum efficiency; CE is the current efficiency; P.E. is the power efficiency; CIE(x,y) are the x and y color coordinates according to the C.I.E. chromaticity scale (Commission Internationale de L'Eclairage, 1931).

Examples 4 and 5 and Comparative Example D

This example illustrates the use of compounds having Formula I as hole transport material in a device, where the photoactive layer is made by vapor deposition.

In Example 4, the hole transport layer was Compound H12, with a final thickness of 100 nm.

In Example 5, the hole transport layer was Compound H13, with a final thickness of 100 nm.

In Comparative Example D, the hole transport layer was compound HT-A, with a final thickness of 100 nm.

The photoactive layer contained Host-1 and Dopant-2 in a weight ratio of 6:1, with a final thickness of 38 nm.

The results are given in Table 4.

TABLE 4

Device results

| Ex. | HTL | Voltage @ 20 mA/cm2 (V) | EQE (%) | CE (cd/A) | P.E. (lm/W) | CIE (x, y) |
|---|---|---|---|---|---|---|
| 4 | H12 | 5.2 | 8.8 | 8.4 | 5.1 | 0.135 0.112 |
| 5 | H13 | 4.4 | 8.6 | 8.0 | 5.7 | 0.136 0.109 |
| Comp. D | HT-A | 4.2 | 8.7 | 7.9 | 5.8 | 0.138 0.104 |

All data @ 1000 nits. HTL is the hole transport layer; EQE is the external quantum efficiency; CE is the current efficiency; P.E. is the power efficiency; CIE(x,y) are the x and y color coordinates according to the C.I.E. chromaticity scale (Commission Internationale de L'Eclairage, 1931).

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. An organic electronic device comprising an anode, a cathode, and a photoactive layer therebetween, and further comprising a hole transport layer comprising a compound having Formula I

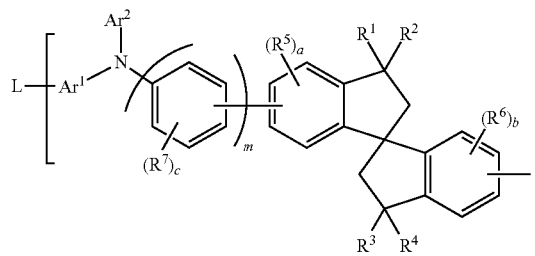

Formula I wherein:
Ar$^1$ and Ar$^3$ are the same or different and are aryl groups;
Ar$^2$ and Ar$^4$ are the same or different and are aryl groups;
L is the same or different at each occurrence and is selected from the group consisting of H, D, halogen, aryl, arylamino, crosslinkable groups, deuterated aryl, deuterated arylamino, and deuterated crosslinkable groups;
R$^1$-R$^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
R$^5$-R$^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent R$^5$-R$^8$ groups can be joined together to form an aromatic ring;
a and b are the same or different and are an integer from 0-3;
c and d are the same or different at each occurrence and are an integer from 0-4;
m and q are the same or different and are an integer from 1-6; and
n is an integer greater than 0.

2. The device of claim 1, wherein Ar$^1$-Ar$^4$ are aryl groups having no fused rings.

3. The device of claim 1, wherein one or both of Ar$^1$ and Ar$^3$ has Formula a

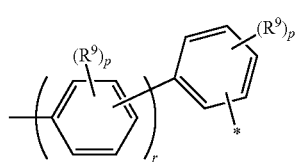

Formula a where:
R$^9$ is the same or different at each occurrence and is selected from the group consisting of D, alkyl, alkoxy, siloxane and silyl;
p is the same or different at each occurrence and is an integer from 0-4;
r is an integer from 1 to 5; and
* indicates the point of attachment to L.

4. The device of claim 1, wherein one or both of Ar$^2$ and Ar$^4$ has Formula d Formula d where:
R$^9$ is the same or different at each occurrence and is selected from the group consisting of D, alkyl, alkoxy, siloxane and silyl;
p is the same or different at each occurrence and is an integer from 0-4;
q is an integer from 0-5; and
r is an integer from 1 to 5.

5. The device of claim 1, wherein one or more of R$^1$-R$^4$ are alkyl groups or deuterated alkyl groups having 1-5 carbons.

6. The device of claim 1, wherein one or more of R$^1$-R$^4$ are selected from the group consisting of phenyl, biphenyl, substituted derivatives thereof, and deuterated analogs thereof.

7. The device of claim 1, wherein the compound has Formula I-b or Formula I-c

Formula I-b

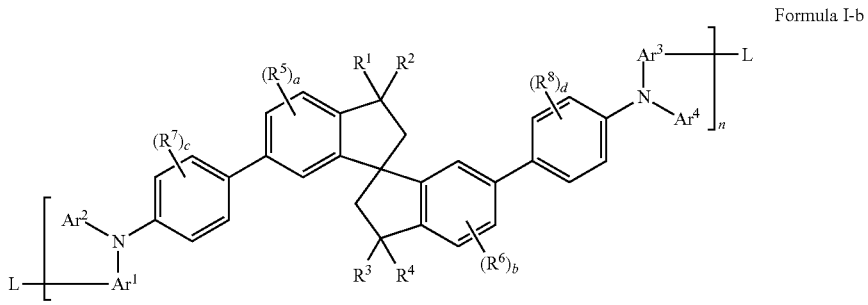

Formula I-c

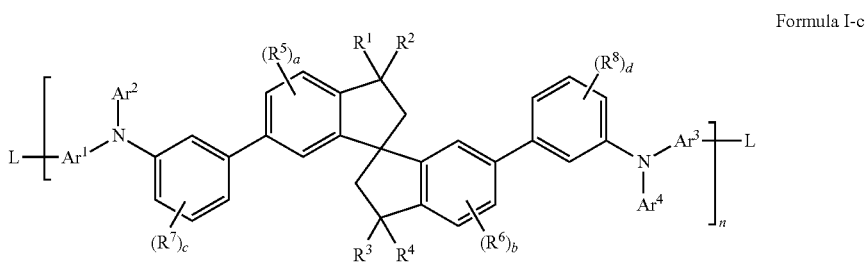

wherein:

Ar¹ and Ar³ are the same or different and are aryl groups;
Ar² and Ar⁴ are the same or different and are aryl groups;
L is the same or different at each occurrence and is selected from the group consisting of H, D, halogen, aryl, arylamino, crosslinkable groups, deuterated aryl, deuterated arylamino, and deuterated crosslinkable groups;
$R^1$-$R^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
$R^5$-$R^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent $R^5$-$R^8$ groups can be joined together to form an aromatic ring;
a and b are the same or different and are an integer from 0-3;
c and d are the same or different at each occurrence and are an integer from 0-4; and
n is an integer greater than 0.

8. The device of claim 1, wherein n>10 and the compound is a polymer.

9. The device of claim 8, wherein $M_n$>20,000.

10. An organic electronic device comprising an anode, a cathode, and a photoactive layer therebetween, and further comprising a hole transport layer comprising a copolymer having at least one monomer unit of Formula I-m Formula I-m

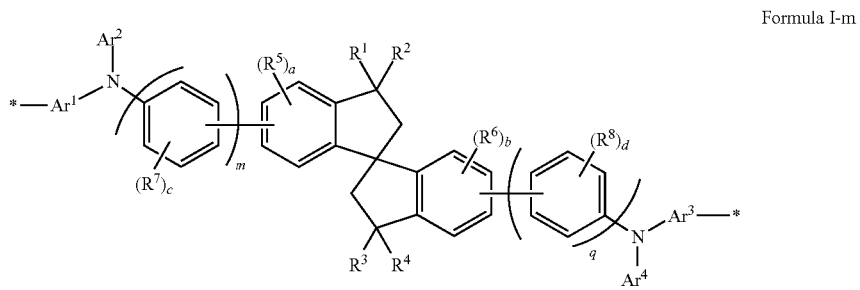

wherein:
Ar¹ and Ar³ are the same or different and are aryl groups;
Ar² and Ar⁴ are the same or different and are aryl groups;
$R^1$-$R^4$ are the same or different and are selected from the group consisting of H, D, alkyl, alkoxy, aryl, aryloxy, silyl, deuterated alkyl, deuterated alkoxy, deuterated aryl, deuterated aryloxy, and deuterated silyl;
$R^5$-$R^8$ are the same or different and are selected from the group consisting of D, F, alkyl, aryl, alkoxy, aryloxy, silyl, crosslinkable groups, deuterated alkyl, deuterated alkoxy, deuterated aryl, deuterated aryloxy, and deuterated silyl, where adjacent $R^5$-$R^8$ groups can be joined together to form an aromatic ring;
a and b are the same or different and are an integer from 0-3;
c and d are the same or different at each occurrence and are an integer from 0-4;
m and q are the same or different and are an integer from 1-6; and
* represents the point of attachment in the copolymer.

11. The device of claim 10, wherein $M_n > 20,000$.
12. An organic electronic device comprising an anode, a cathode, and a photoactive layer therebetween, and further comprising a hole transport layer comprising a compound selected from the group consisting of Compound H2 through Compound H5 and Compound H7 through Compound H18:
Compound H2
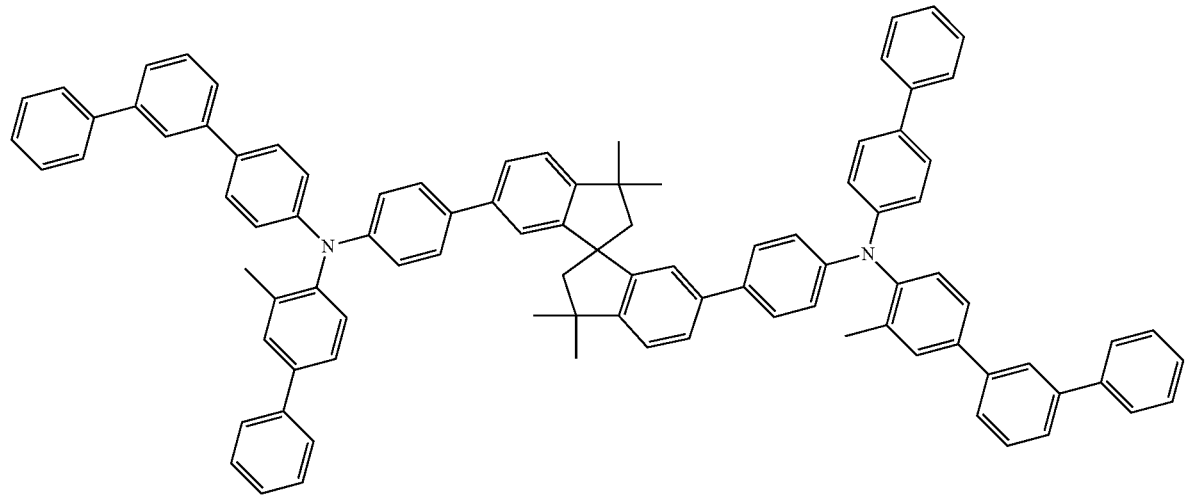
Compound H3
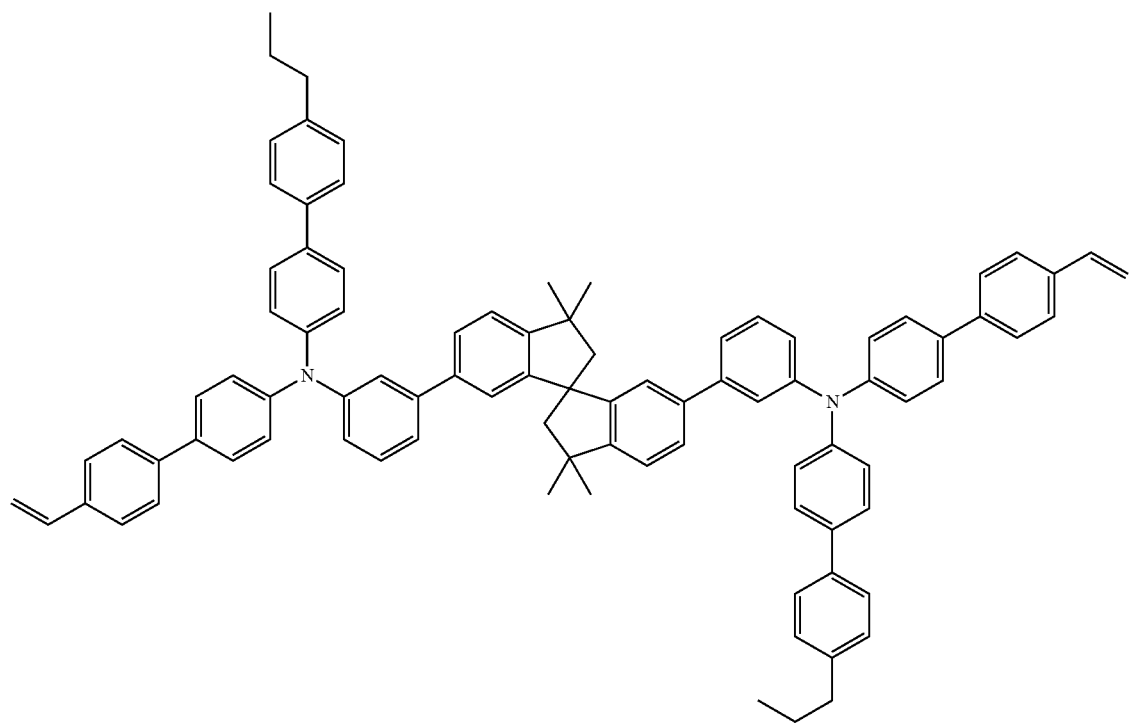

Compound H4
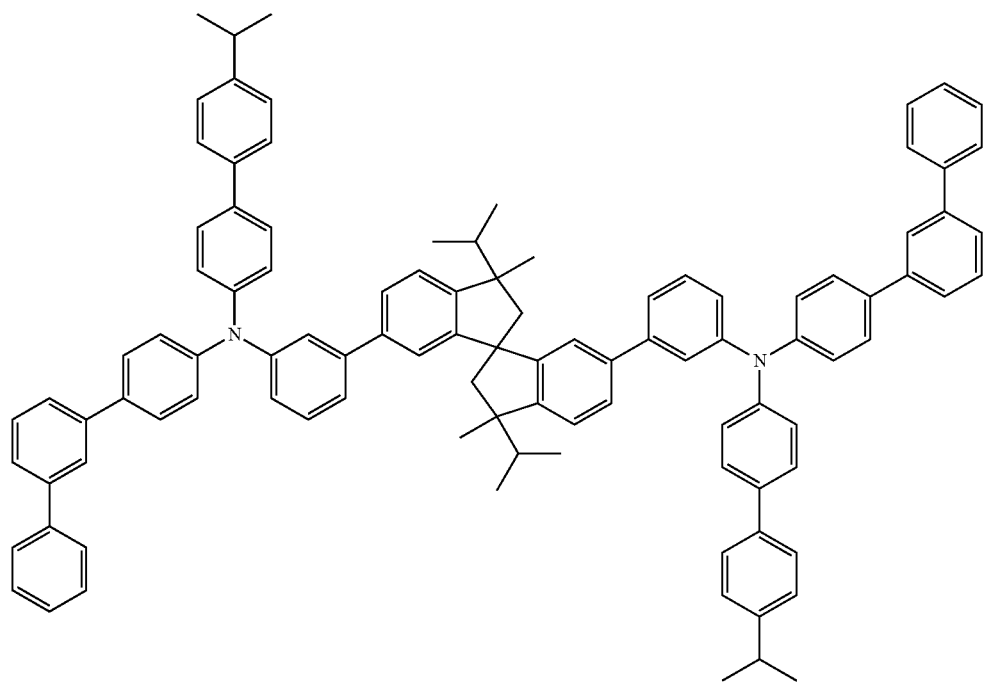
Compound H5
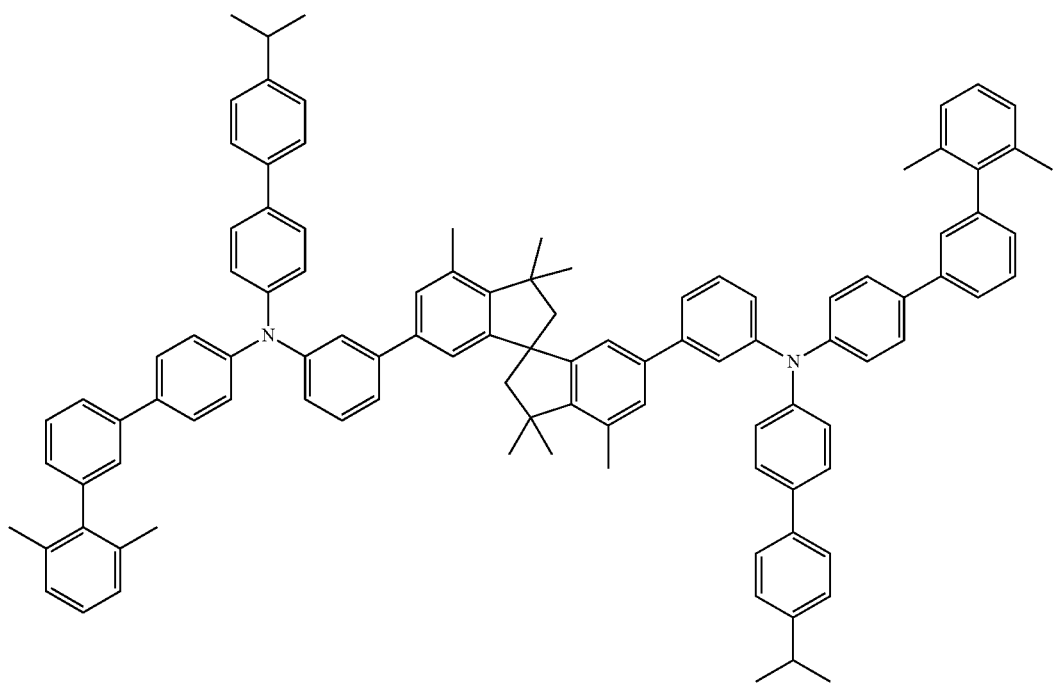

Compound H7
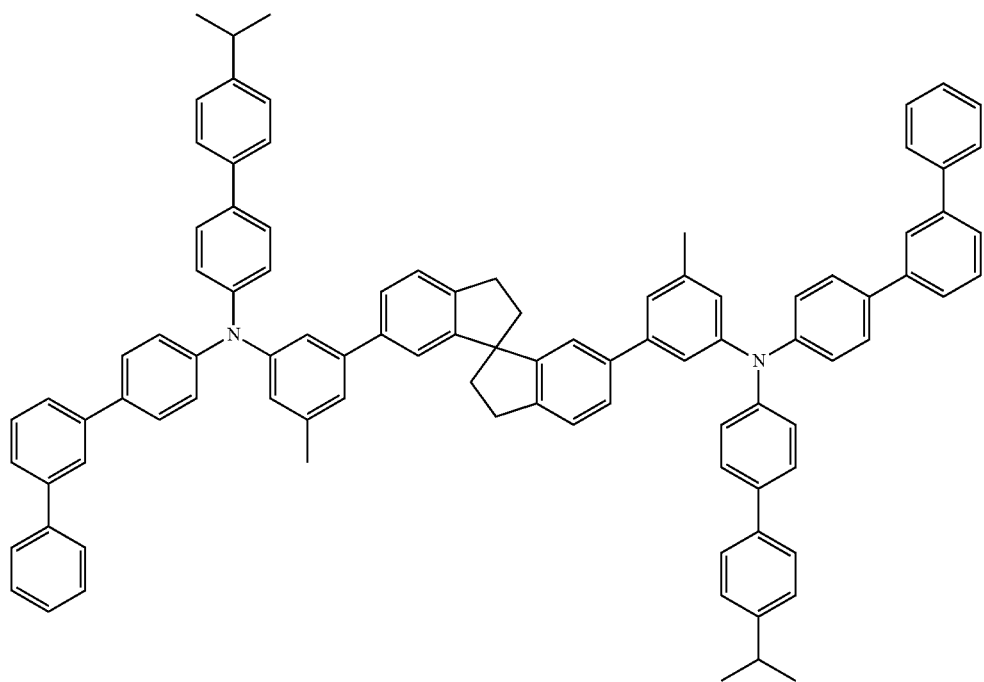
Compound H8
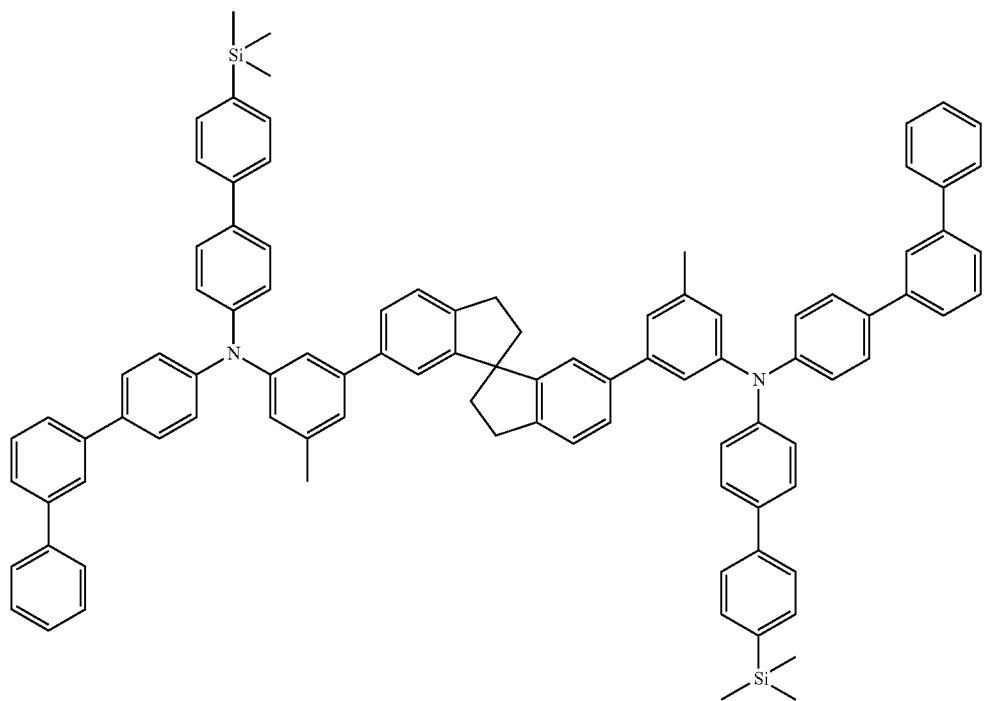

Compound H9
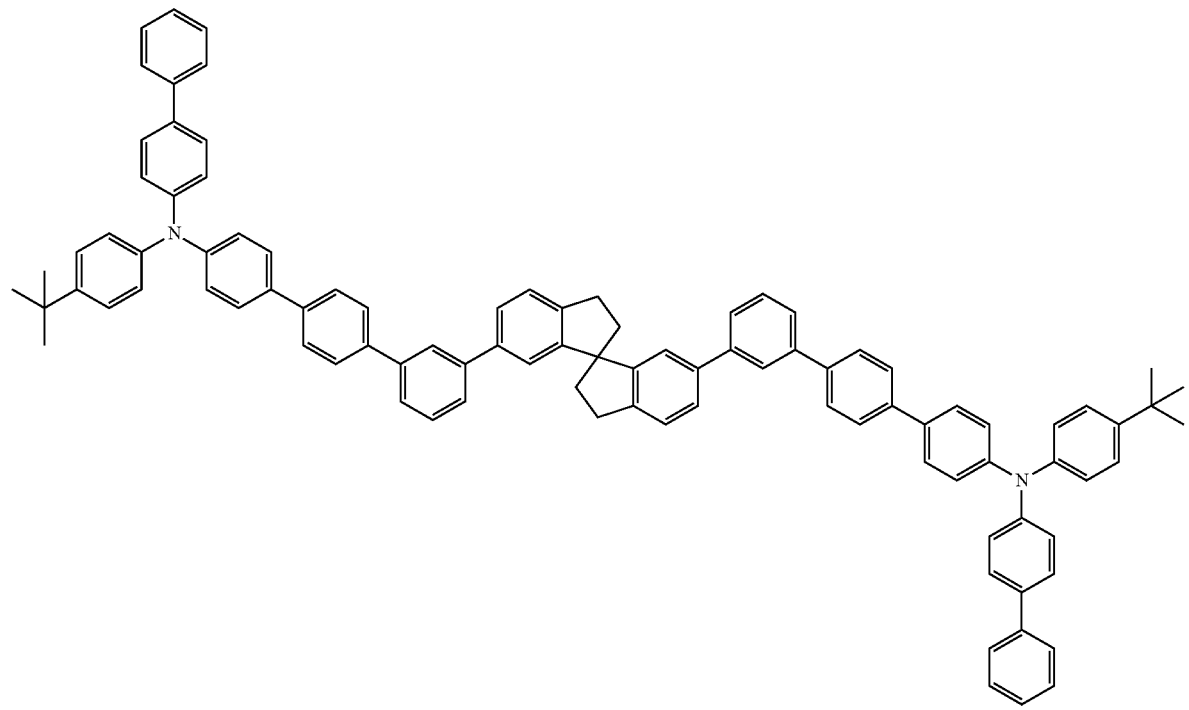
Compound H10
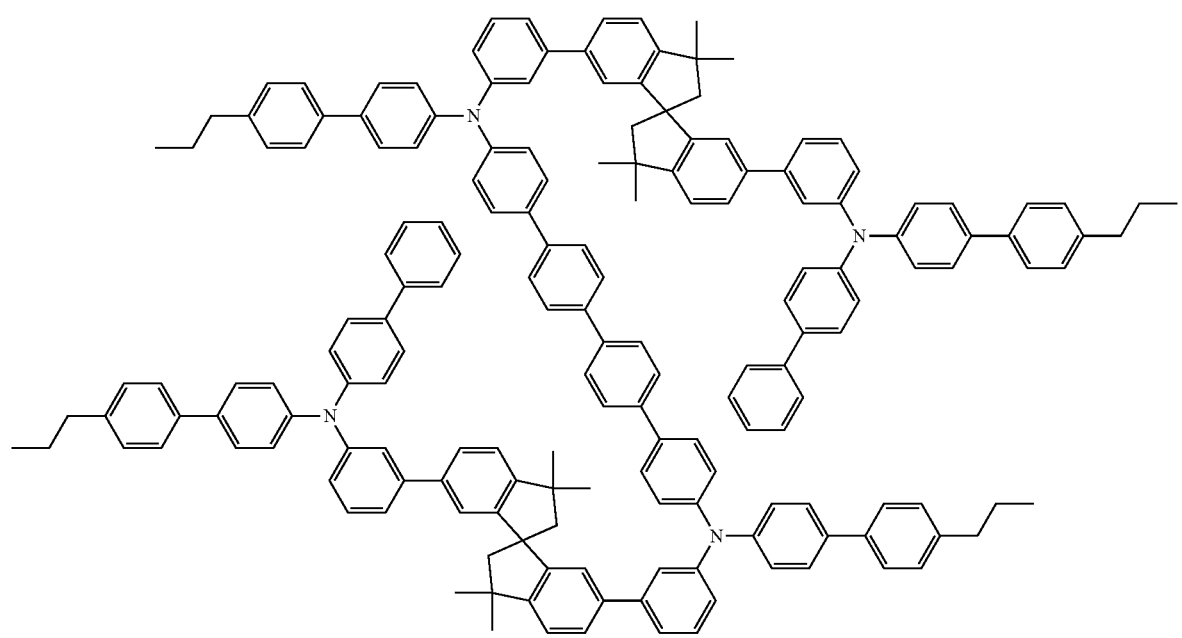

Compound H11
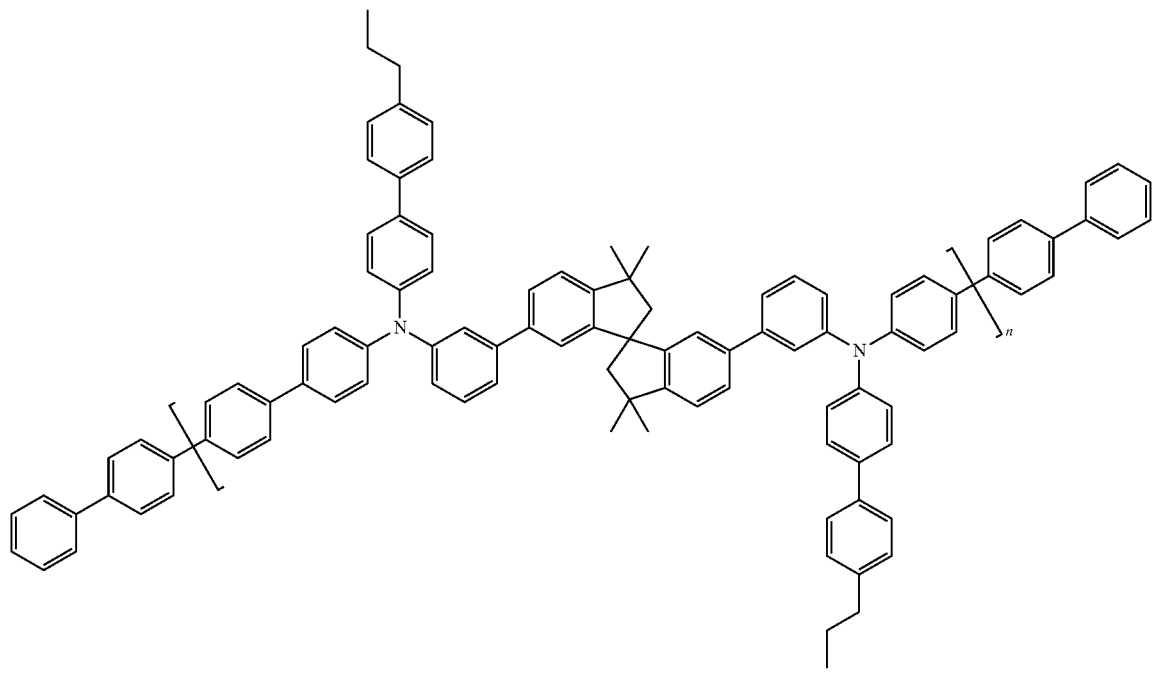
Compound H12
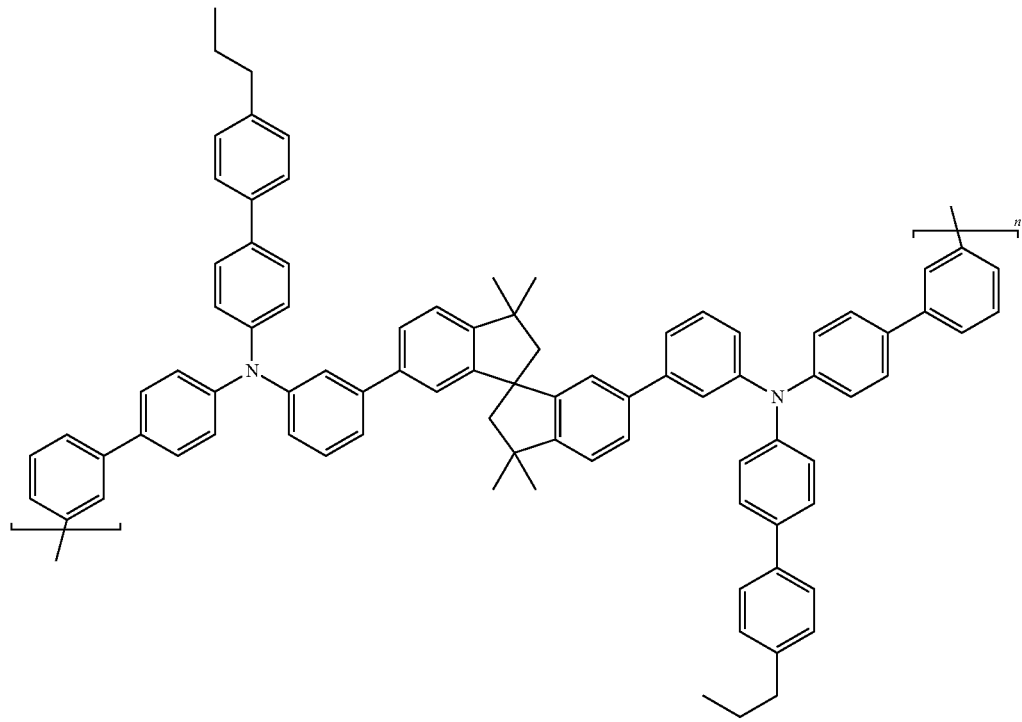

Compound H13
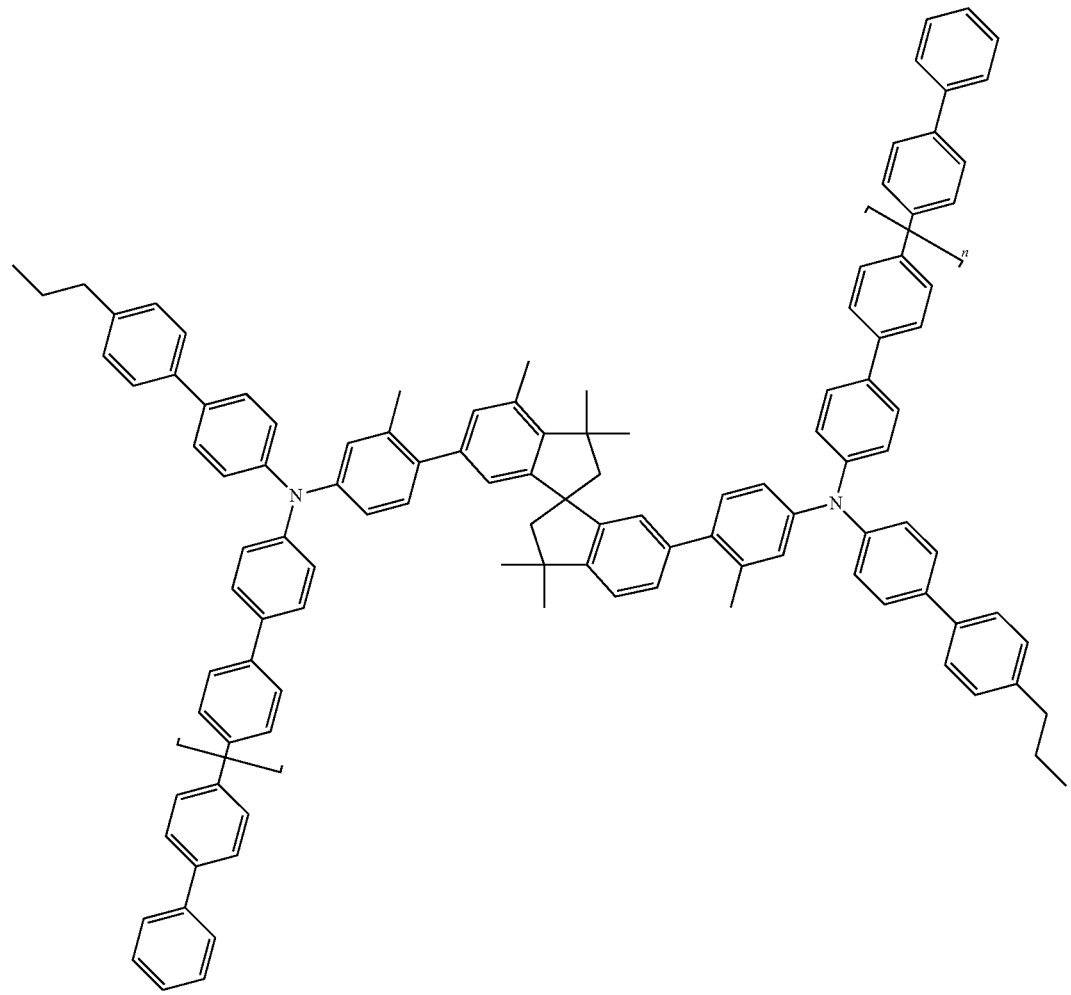
Compound H14
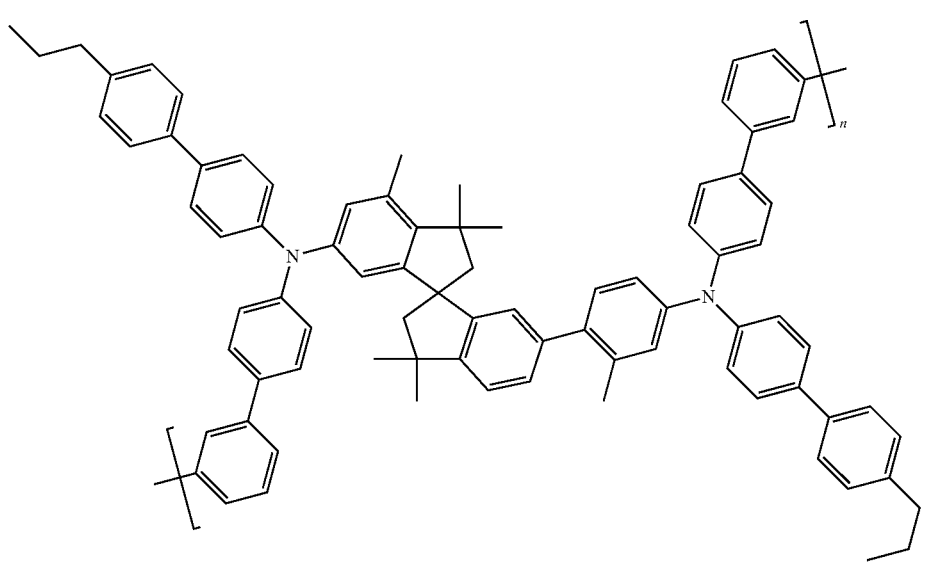

Compound H15
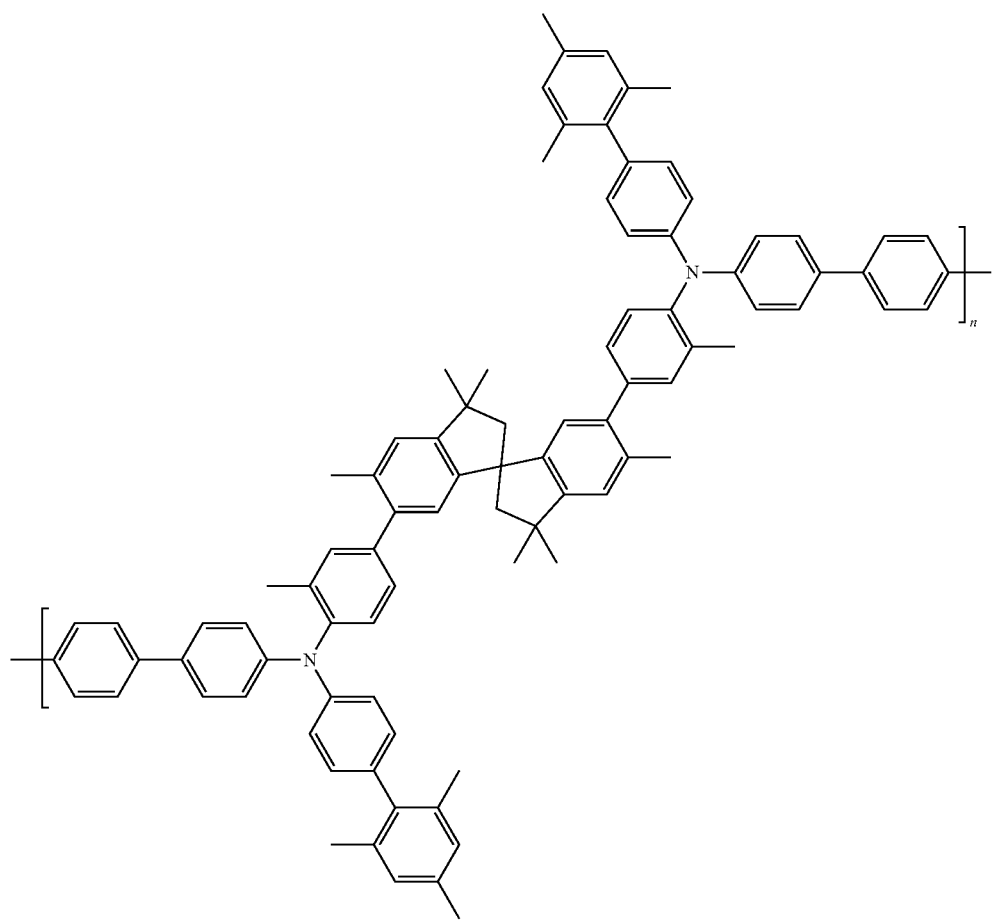
Compound H16
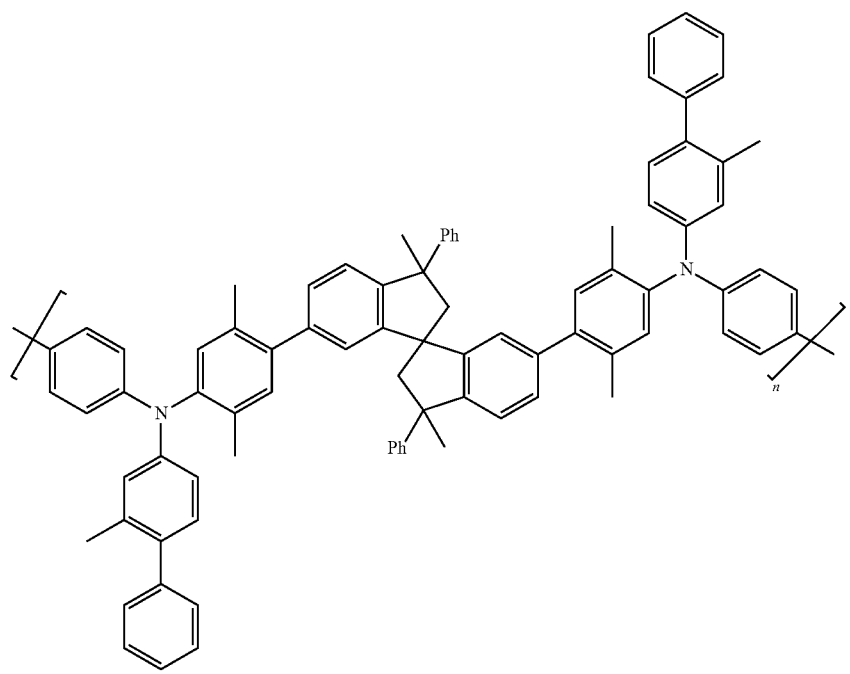

Compound H17
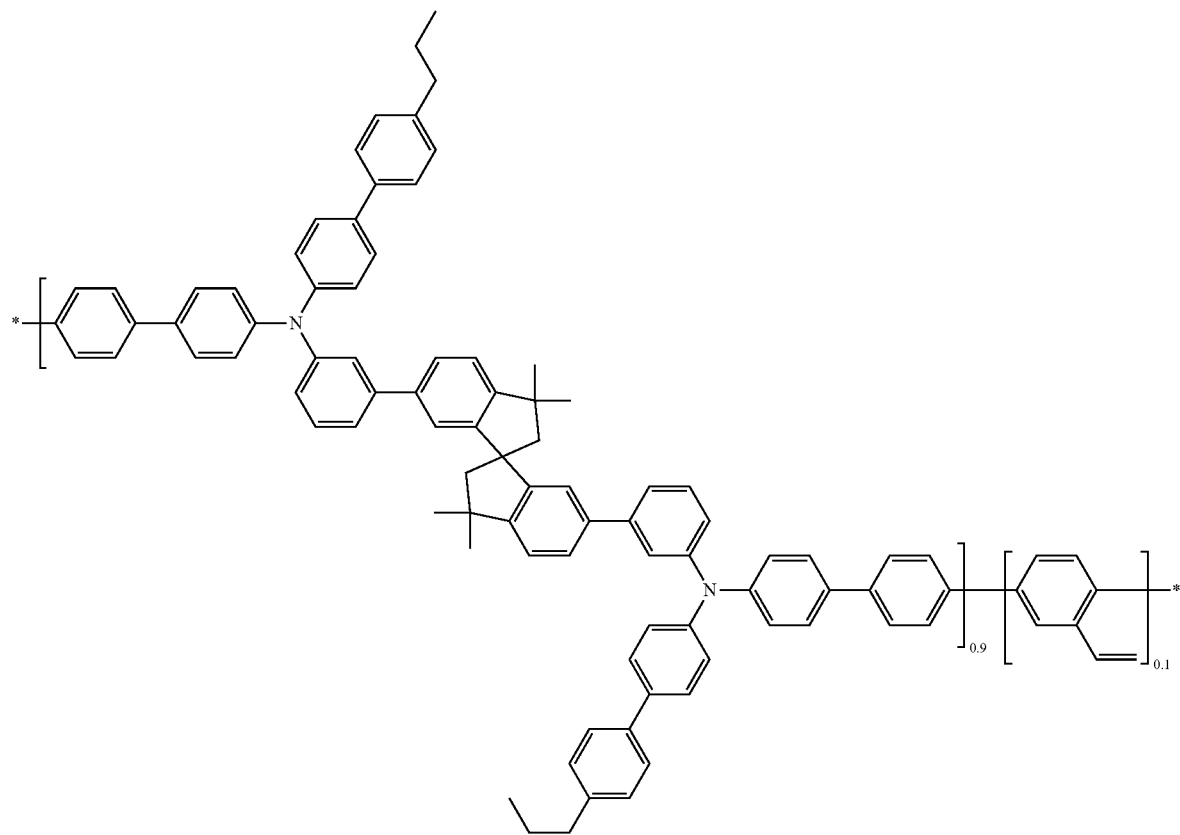
Compound H18
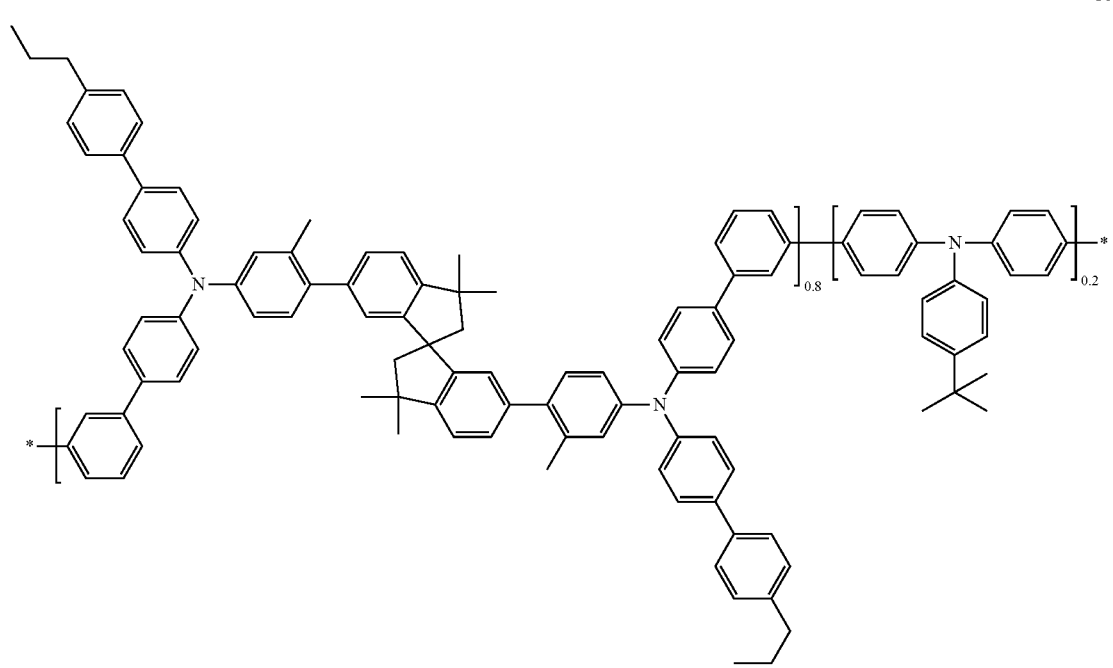
where n is an integer greater than 0, and * indicates a point of attachment.
* * * * *